(12) United States Patent
Pastan et al.

(10) Patent No.: US 10,925,969 B2
(45) Date of Patent: Feb. 23, 2021

(54) ANTI-BCMA POLYPEPTIDES AND PROTEINS

(71) Applicants: The United States of America, as represented by the Secretary, Department of Health and Human Services, Bethesda, MD (US); Sanford Research, Sioux Falls, SD (US)

(72) Inventors: Ira H. Pastan, Potomac, MD (US); Tapan Bera, Frederick, MD (US); Satoshi Nagata, Osaka (JP); Tomoko Ise, Osaka (JP); Yasuhiro Abe, Tokyo (JP)

(73) Assignees: The United States of America, as represented by the Secretary, Department of Health and Human Service, Bethesda, MD (US); Sanford Research, Sioux Falls, SD (US)

( * ) Notice: Subject to any disclaimer, the term of this patent is extended or adjusted under 35 U.S.C. 154(b) by 47 days.

(21) Appl. No.: 15/773,687

(22) PCT Filed: Nov. 10, 2016

(86) PCT No.: PCT/US2016/061320
§ 371 (c)(1),
(2) Date: May 4, 2018

(87) PCT Pub. No.: WO2017/083511
PCT Pub. Date: May 18, 2017

(65) Prior Publication Data
US 2018/0318435 A1 Nov. 8, 2018

Related U.S. Application Data

(60) Provisional application No. 62/257,493, filed on Nov. 19, 2015, provisional application No. 62/255,255, filed on Nov. 13, 2015.

(51) Int. Cl.
| A61K 47/64 | (2017.01) |
| C07K 16/28 | (2006.01) |
| A61K 39/00 | (2006.01) |

(52) U.S. Cl.
CPC .......... *A61K 47/6415* (2017.08); *A61K 39/00* (2013.01); *A61K 47/6425* (2017.08); *C07K 16/2878* (2013.01); *A61K 2039/505* (2013.01); *C07K 2319/03* (2013.01)

(58) Field of Classification Search
None
See application file for complete search history.

(56) References Cited

U.S. PATENT DOCUMENTS

| 4,892,827 A | 1/1990 | Pastan et al. |
| 5,512,658 A | 4/1996 | Pastan et al. |
| 5,602,095 A | 2/1997 | Pastan et al. |
| 5,608,039 A | 3/1997 | Pastan et al. |
| 5,821,238 A | 10/1998 | Pastan et al. |
| 5,854,044 A | 12/1998 | Pastan et al. |
| 8,871,906 B2 | 10/2014 | Pastan et al. |
| 8,907,060 B2 | 12/2014 | Pastan et al. |
| 8,936,792 B2 | 1/2015 | Pastan et al. |
| 9,034,324 B2 | 5/2015 | Kalled et al. |
| 9,206,240 B2 | 12/2015 | Pastan et al. |
| 9,346,859 B2 | 5/2016 | Pastan et al. |
| 9,388,222 B2 | 7/2016 | Pastan et al. |
| 2015/0099707 A1 | 4/2015 | Pastan et al. |
| 2015/0284467 A1 | 10/2015 | Lipp et al. |

FOREIGN PATENT DOCUMENTS

| JP | 2012-167112 A | 9/2012 |
| JP | 2015-057383 A | 3/2015 |
| WO | WO 2006/122786 A2 | 11/2006 |
| WO | WO 2010/061193 A2 | 6/2010 |
| WO | WO 2012/163805 A1 | 12/2012 |
| WO | WO 2013/154760 A1 | 10/2013 |
| WO | WO 2014/089335 A2 | 6/2014 |
| WO | WO 2016/014565 A2 | 1/2016 |

OTHER PUBLICATIONS

Bendig (Methods: A Companion to Methods in Enzymology 1995; 8:83-93).*
Kussie et al, Journal of Immunology, 152:146-152, 1994.*
Chen et al , The EMBO Journal 14(12):2784-2794, 1995.*
Bera et al., "Recombinant immunotoxins targeting B-cell maturation antigen are cytotoxic to myeloma cell lines and myeloma cells from patients" and Supplementary Material, *Leukemia*, 32(2): 569-572 (2018).
Ali et al., "T cells expressing an anti-B-cell maturation antigen chimeric antigen receptor cause remissions of multiple myeloma," *Blood*, 128(13): 1688-1700 (2016).
Carpenter et al., "B-cell Maturation Antigen is a Promising Target for Adoptive T-cell Therapy of Multiple Myeloma," *Clin. Cancer Res.*, 19(8): 2040-2060 (2013).
International Bureau, International Search Report and Written Opinion in International Application No. PCT/US2016/061320, dated Mar. 3, 2017.
Maus et al., "Zoom Zoom: Racing CARs for Multiple Myeloma," *Clin. Cancer Res.*, 19(8): 1917-1919 (2013).

(Continued)

*Primary Examiner* — Patricia Duffy
(74) *Attorney, Agent, or Firm* — Leydig, Voit & Mayer

(57) ABSTRACT

Polypeptides and proteins that specifically bind to and immunologically recognize B-Cell Maturation Antigen (BCMA) are disclosed. Chimeric antigen receptors (CARs), anti-BCMA binding moieties, nucleic acids, recombinant expression vectors, host cells, populations of cells, pharmaceutical compositions, and conjugates relating to the polypeptides and proteins are also disclosed. Methods of detecting the presence of cancer and methods of treating or preventing cancer are also disclosed.

25 Claims, 14 Drawing Sheets
Specification includes a Sequence Listing.

(56) References Cited

OTHER PUBLICATIONS

Oden et al., "Potent anti-tumor response by targeting B cell maturation antigen (BCMA) in a mouse model of multiple myeloma," and Supplementary Materials, *Mol. Oncol.*, 9(7): 1348-1358 (2015).

Ramadoss et al., "An Anti-B Cell Maturation Antigen Bispecific Antibody for Multiple Myeloma," *J. Am. Chem. Soc.*, 137(16): 5288-5291 (2015).

Ryan et al., "Antibody targeting of B-cell maturation antigen on malignant plasma cells," *Mol. Cancer Ther.*, 6(11): 3009-3018 (2007).

Tai et al., "Novel anti-B-cell maturation antigen antibody-drug conjugate (GSK2857916) selectively induces killing of multiple myeloma," *Blood*, 123(20): 3128-3738 (2014).

Tai et al., "Targeting B-cell maturation antigen in multiple myeloma," *Immunotherapy*, 7(11): 1187-1199 (2015).

Van Rhee, "Engineering more efficacious antibody therapy for myeloma," *Blood*, 123(20): 3062-3063 (2014).

Wu et al., "An analysis of the Sequences of the Variable Regions of Bence Jones Proteins and Myeloma Light Chains and Their Implications for Antibody Complementarity," *J. Exp. Med.*, 132: 211-250 (1970).

"ForteBio, Biologics by Molecular Devices: BLItz$^+$System," *ForteBio* (2019).

Japanese Patent Office, Notice of Reasons for Refusal—Japanese Patent Application No. 544769/2018, dated Oct. 13, 2020.

\* cited by examiner

SEQUENCE LISTING

<160> NUMBER OF SEQ ID NOS: 18

<210> SEQ ID NO 1
<211> LENGTH: 8
<212> TYPE: PRT
<213> ORGANISM: Artificial Sequence

```
<220> FEATURE:
<223> OTHER INFORMATION: Synthetic

<400> SEQUENCE: 1

Gly Asn Thr Leu Thr Asn Tyr Val
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Ile Leu Pro Tyr Asn Asp Leu Thr
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic

<400> SEQUENCE: 3

Thr Arg Trp Asp Trp Asp Gly Phe Phe Asp Pro
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Gln Ser Leu Val His Ser Asn Gly Asn Thr His
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Synthetic

<400> SEQUENCE: 5

Ser Val Ser
1

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Ser Gln Thr Ser His Ile Pro Tyr Thr
1               5

<210> SEQ ID NO 7
<211> LENGTH: 8
<212> TYPE: PRT
<213> ORGANISM: Artificial Sequence
<220> FEATURE:
```

<223> OTHER INFORMATION: Synthetic

<400> SEQUENCE: 7

Gly Tyr Thr Phe Thr Glu Tyr Thr
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Ile Tyr Pro Asp Asn Tyr Asn Ile
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic

<400> SEQUENCE: 9

Ala Asn His Asp Phe Phe Val Phe
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic

<400> SEQUENCE: 10

Gln Asp Ile Ser Asn His
1               5

<210> SEQ ID NO 11
<211> LENGTH: 3
<212> TYPE: PRT
<213> ORGANISM: Artificial Sequence
<220> FEATURE:
<223> OTHER INFORMATION: Synthetic

<400> SEQUENCE: 11

Tyr Thr Ser
1

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

His Gln Gly Asn Thr Leu Pro Pro Thr
1               5

<210> SEQ ID NO 13
<211> LENGTH: 121
<212> TYPE: PRT
<213> ORGANISM: Artificial Sequence
<220> FEATURE:
<223> OTHER INFORMATION: Synthetic

<400> SEQUENCE: 13

Met Glu Val Gln Leu Gln Gln Ser Gly Pro Glu Leu Val Lys Pro Gly
1               5                   10                  15

Ala Ser Val Lys Met Ser Cys Lys Ala Ser Gly Asn Thr Leu Thr Asn
            20                  25                  30

Tyr Val Ile His Trp Met Lys Gln Met Pro Gly Gln Gly Leu Asp Trp
        35                  40                  45

Ile Gly Tyr Ile Leu Pro Tyr Asn Asp Leu Thr Lys Tyr Asn Glu Lys
50                  55                  60

Phe Thr Gly Lys Ala Thr Leu Thr Ser Asp Lys Ser Ser Ser Ser Ala
65                  70                  75                  80

Tyr Met Glu Leu Asn Ser Leu Thr Ser Glu Asp Ser Ala Val Tyr Tyr
                85                  90                  95

Cys Thr Arg Trp Asp Trp Asp Gly Phe Phe Asp Pro Trp Gly Gln Gly
            100                 105                 110

Thr Thr Leu Thr Val Ser Ser Ala Ser
        115                 120

<210> SEQ ID NO 14
<211> LENGTH: 114
<212> TYPE: PRT
<213> ORGANISM: Artificial Sequence
<220> FEATURE:
<223> OTHER INFORMATION: Synthetic

<400> SEQUENCE: 14

Met Asp Ile Val Met Thr Gln Ser Pro Leu Ser Leu Pro Val Ser Leu
1               5                   10                  15

Gly Asp Gln Ala Ser Ile Ser Cys Arg Ser Thr Gln Ser Leu Val His
            20                  25                  30

Ser Asn Gly Asn Thr His Leu His Trp Tyr Leu Gln Arg Pro Gly Gln
        35                  40                  45

Ser Pro Lys Leu Leu Ile Tyr Ser Val Ser Asn Arg Phe Ser Glu Val
50                  55                  60

Pro Asp Arg Phe Ser Ala Ser Gly Ser Gly Thr Asp Phe Thr Leu Lys
65                  70                  75                  80

Ile Ser Arg Val Glu Ala Glu Asp Leu Gly Val Tyr Phe Cys Ser Gln
                85                  90                  95

Thr Ser His Ile Pro Tyr Thr Phe Gly Gly Gly Thr Lys Leu Glu Ile
            100                 105                 110

Lys Arg

<210> SEQ ID NO 15
<211> LENGTH: 118
<212> TYPE: PRT
<213> ORGANISM: Artificial Sequence
<220> FEATURE:
<223> OTHER INFORMATION: Synthetic

<400> SEQUENCE: 15

Met Glu Val Gln Leu Gln Gln Ser Gly Pro Glu Leu Val Lys Pro Gly
1               5                   10                  15

Ala Ser Val Lys Ile Ser Cys Lys Thr Ser Gly Tyr Thr Phe Thr Glu
            20                  25                  30

Tyr Thr Ile Asn Trp Val Lys Gln Ser His Gly Lys Ser Leu Glu Trp
        35                  40                  45

```
Ile Gly Asp Ile Tyr Pro Asp Asn Tyr Asn Ile Arg Tyr Asn Gln Lys
        50                  55                  60

Phe Lys Gly Lys Ala Thr Leu Thr Val Asp Lys Ser Ser Ser Thr Ala
65                  70                  75                  80

Tyr Met Glu Leu Arg Ser Leu Ser Ser Glu Asp Ser Ala Ile Tyr Tyr
                85                  90                  95

Cys Ala Asn His Asp Phe Phe Val Phe Trp Gly Gln Gly Thr Leu Val
                100                 105                 110

Thr Val Ser Ala Ala Lys
            115

<210> SEQ ID NO 16
<211> LENGTH: 109
<212> TYPE: PRT
<213> ORGANISM: Artificial Sequence
<220> FEATURE:
<223> OTHER INFORMATION: Synthetic

<400> SEQUENCE: 16

Met Asp Ile Gln Met Thr Gln Ala Thr Ser Ser Leu Ser Ala Ser Leu
1               5                   10                  15

Gly Asp Arg Val Thr Ile Asn Cys Arg Thr Ser Gln Asp Ile Ser Asn
            20                  25                  30

His Leu Asn Trp Tyr Gln Gln Lys Pro Asp Gly Thr Val Lys Leu Leu
        35                  40                  45

Ile Tyr Tyr Thr Ser Arg Leu Gln Ser Gly Val Pro Ser Arg Phe Ser
    50                  55                  60

Gly Ser Gly Ser Gly Thr Asp Tyr Ser Leu Thr Ile Ser Asn Leu Glu
65                  70                  75                  80

Gln Glu Asp Ile Gly Thr Tyr Phe Cys His Gln Gly Asn Thr Leu Pro
                85                  90                  95

Pro Thr Phe Gly Gly Gly Thr Lys Leu Glu Ile Lys Arg
                100                 105

<210> SEQ ID NO 17
<211> LENGTH: 3
<212> TYPE: PRT
<213> ORGANISM: Artificial Sequence
<220> FEATURE:
<223> OTHER INFORMATION: Synthetic

<400> SEQUENCE: 17

Gly Gly Ser
1

<210> SEQ ID NO 18
<211> LENGTH: 12
<212> TYPE: PRT
<213> ORGANISM: Artificial Sequence
<220> FEATURE:
<223> OTHER INFORMATION: Synthetic

<400> SEQUENCE: 18

Gly Gly Ser Gly Gly Ser Gly Gly Ser Gly Gly Ser
1               5                   10
```

ANTI-BCMA POLYPEPTIDES AND PROTEINS

CROSS-REFERENCE TO RELATED APPLICATIONS

This patent application is a U.S. national phase of PCT/US2016/061320, filed Nov. 10, 2016, which claims the benefit of U.S. Provisional Patent Application Nos. 62/255,255, filed Nov. 13, 2015, and 62/257,493, filed Nov. 19, 2015, each of which is incorporated by reference in its entirety herein.

STATEMENT REGARDING FEDERALLY SPONSORED RESEARCH OR DEVELOPMENT

This invention was made with Government support under project number Z01BC008753 by the National Institutes of Health, National Cancer Institute. The Government has certain rights in the invention.

INCORPORATION-BY-REFERENCE OF MATERIAL SUBMITTED ELECTRONICALLY

This invention was made with Government support under project number Z01BC008753 by the National Institutes of Health, National Cancer Institute and grant number P20 GM103548 awarded by the National Institutes of Health, National Institute of General Medical Sciences. The Government has certain rights in the invention.

BACKGROUND OF THE INVENTION

Cancer is a public health concern. Despite advances in treatments such as chemotherapy, the prognosis for many cancers, including multiple myeloma, may be poor. Accordingly, there exists an unmet need for additional treatments for cancer, particularly multiple myeloma.

BRIEF SUMMARY OF THE INVENTION

An embodiment of the invention provides a polypeptide comprising the complementarity determining region (CDR) sequences of antibody BM24 or BM306.

Another embodiment of the invention provides a polypeptide comprising the amino acid sequences of (a) SEQ ID NOs: 1-6 or (b) SEQ ID NO: 7-12.

Further embodiments of the invention provide related anti-BCMA binding moieties, nucleic acids, recombinant expression vectors, host cells, populations of cells, conjugates, and pharmaceutical compositions relating to the polypeptides and proteins of the invention.

Additional embodiments of the invention provide methods of detecting the presence of cancer in a mammal and methods of treating or preventing cancer in a mammal.

DETAILED DESCRIPTION OF THE INVENTION

Figure 1:
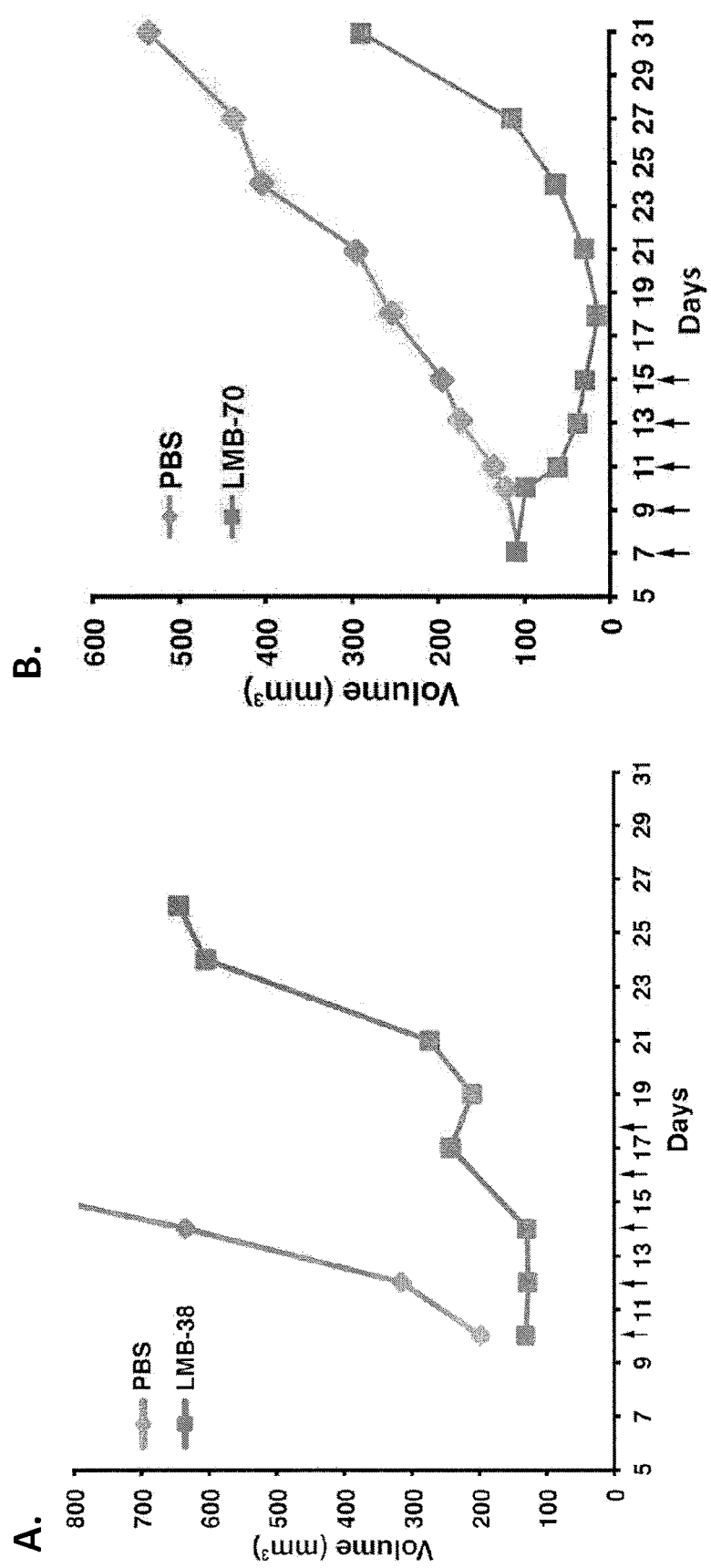
FIG. 1A is a graph showing the tumor volume ($mm^3$) in mice treated with PBS (diamonds) or LMB-38 (squares) at various time points (days) after the mice were injected with tumor cells. The arrows indicate the days on which immunotoxin was administered to the mice.
FIG. 1B is a graph showing the tumor volume ($mm^3$) in mice treated with PBS (diamonds) or LMB-70 (squares) at various time points (days) after the mice were injected with tumor cells. The arrows indicate the days on which immunotoxin was administered to the mice.

An embodiment of the invention provides polypeptides and proteins comprising an antigen binding domain of an anti-B-cell Maturation Antigen (BCMA) antibody. The polypeptides and proteins advantageously specifically recognize and bind to BCMA (also referred to as CD269) with high affinity. BCMA is a member of the tumor necrosis factor receptor (TNFR) superfamily. BCMA binds B-cell activating factor (BAFF) and a proliferation inducing ligand (APRIL). Among nonmalignant cells, BCMA has been reported to be expressed mostly in plasma cells and subsets of mature B-cells. BCMA RNA has been detected in multiple myeloma cells, and BCMA protein has been detected on the surface of plasma cells from multiple myeloma patients.

BCMA is expressed or overexpressed by various human cancers. Examples of cancers that express or overexpress BCMA include, but are not limited to, Burkitt's lymphoma, diffuse large B-cell lymphoma (DLBCL) lymphoma, acute lymphocytic leukemia (ALL) lymphoma, Hodgkin's lymphoma and multiple myeloma. Without being bound to a particular theory or mechanism, it is believed that by specifically recognizing and binding to BCMA, the inventive polypeptides and proteins may, advantageously, target BCMA-expressing cancer cells. In an embodiment of the invention, the inventive polypeptides and proteins may elicit an antigen-specific response against BCMA. Accordingly, without being bound to a particular theory or mechanism, it is believed that by specifically recognizing and binding BCMA, the inventive proteins and polypeptides may provide for one or more of the following: detecting BCMA-expressing cancer cells, targeting and destroying BCMA-expressing cancer cells, reducing or eliminating cancer cells, facilitating infiltration of immune cells and/or effector molecules to tumor site(s), and enhancing/extending anti-cancer responses.

The term "polypeptide," as used herein, includes oligopeptides and refers to a single chain of amino acids connected by one or more peptide bonds. The polypeptide may comprise one or more variable regions (e.g., two variable regions) of an antigen binding domain of an anti-BCMA antibody, each variable region comprising a complementarity determining region (CDR) 1, a CDR2, and a CDR3. In an embodiment of the invention, the polypeptide comprises CDR sequences of antibody BM24 or BM306. The CDR binding sequences may be determined by methods known in the art such as, for example, the methodology of the international ImMunoGeneTics information system (IMGT) or Kabat (Wu and Kabat *J. Exp. Med.*, 132: 211-250 (1970)).

Preferably, a first variable region comprises a CDR1 comprising the amino acid sequence of SEQ ID NO: 1 or 7 (CDR1 of first variable region), a CDR2 comprising the amino acid sequence of SEQ ID NO: 2 or 8 (CDR2 of first variable region), and a CDR3 comprising the amino acid sequence of SEQ ID NO: 3 or 9 (CDR3 of first variable region), and the second variable region comprises a CDR1 comprising the amino acid sequence of SEQ ID NO: 4 or 10 (CDR1 of second variable region), a CDR2 comprising the amino acid sequence of SEQ ID NO: 5 or 11 (CDR2 of second variable region), and a CDR3 comprising the amino acid sequence of SEQ ID NO: 6 or 12 (CDR3 of second variable region). In this regard, the inventive polypeptide can comprise the amino acid sequences of SEQ ID NOs: (a) 1-3, (b) SEQ ID NOs: 4-6, (c) SEQ ID NOs: 7-9, (d) SEQ ID NOs: 10-12, (e) SEQ ID NOs: 1-6, or (f) SEQ ID NOs: 7-12. Preferably, an embodiment of the invention provides a polypeptide comprising the amino acid sequences of (i) SEQ ID NOs: 1-6 or (ii) SEQ ID NOs: 7-12.

In an embodiment, the polypeptides each comprise one or more variable regions (e.g., first and second variable regions) of an antigen binding domain of an anti-BCMA antibody, each comprising the CDRs as described above. For example, the polypeptide may comprise the heavy chain variable region and the light chain variable region of antibody BM24 or BM306. The first variable region may comprise the amino acid sequence of SEQ ID NO: 13 or 15. The second variable region may comprise the amino acid sequence of SEQ ID NO: 14 or 16. Accordingly, in an embodiment of the invention, the polypeptide comprises the amino acid sequence of (a) SEQ ID NO: 13, (b) SEQ ID NO: 14, (c) SEQ ID NO: 15, (d) SEQ ID NO: 16, (e) SEQ ID NOs: 13 and 14, or (f) SEQ ID NOs: 15 and 16. Preferably, the polypeptide comprises the amino acid sequences of (i) SEQ ID NOs: 13 and 14 or (ii) SEQ ID NOs: 15 and 16. In an embodiment of the invention, the first variable region is the heavy chain of an anti-BCMA antibody and the second variable region is the light chain of an anti-BCMA antibody.

In an embodiment of the invention, the variable regions of the polypeptide may be joined by a linker. The linker may comprise any suitable amino acid sequence. In an embodiment of the invention, the linker is a Gly/Ser linker from about 1 to about 100, from about 3 to about 20, from about 5 to about 30, from about 5 to about 18, or from about 3 to about 8 amino acids in length and consists of glycine and/or serine residues in sequence. Accordingly, the Gly/Ser linker may consist of glycine and/or serine residues. In some embodiments, the Gly/Ser linker is a peptide of the formula: $(Xaa1)_n$, wherein each amino acid residue Xaa1 is selected independently from glycine and serine and n is an integer from 3 to 15. Preferably, the Gly/Ser linker comprises the amino acid sequence of SEQ ID NO: 17 or 18.

The invention further provides a protein comprising at least one of the polypeptides described herein. By "protein" is meant a molecule comprising one or more polypeptide chains.

The protein of the invention can comprise a first polypeptide chain comprising the amino acid sequences of (i) SEQ ID NOs: 1-3 or (ii) SEQ ID NOs: 7-9 and a second polypeptide chain comprising the amino acid sequences of (i) SEQ ID NOs: 4-6, (ii) SEQ ID NOs: 10-12. In this regard, the protein may comprise a first polypeptide chain comprising (i) the amino acid sequences of SEQ ID NOs: 1-3 and a second polypeptide chain comprising the amino acid sequences of SEQ ID NOs: 4-6 or (ii) a first polypeptide chain comprising the amino acid sequences of SEQ ID NOs: 7-9 and a second polypeptide chain comprising the amino acid sequences of SEQ ID NOs: 10-12. The protein of the invention can, for example, comprise a first polypeptide chain comprising the amino acid sequence of SEQ ID NO: 13 or 15 and a second polypeptide chain comprising the amino acid sequence of SEQ ID NO: 14 or 16. In this regard, the protein may comprise a first polypeptide chain comprising (i) the amino acid sequence of SEQ ID NO: 13 and a second polypeptide chain comprising the amino acid sequence of SEQ ID NO: 14 or (ii) a first polypeptide chain comprising the amino acid sequence of SEQ ID NO: 15 and a second polypeptide chain comprising the amino acid sequence of SEQ ID NO: 16.

The protein may further comprise a linker as described herein with respect to other aspects of the invention.

The protein of the invention can be, for example, a fusion protein. If, for example, the protein comprises a single polypeptide chain comprising (i) SEQ ID NO: 13 or 15 and (ii) SEQ ID NO: 14 or 16, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods.

It is contemplated that the polypeptides and proteins of the invention may be useful as anti-BCMA binding moieties. In this regard, an embodiment of the invention provides an anti-BCMA binding moiety comprising any of the polypeptides or proteins described herein. In an embodiment of the invention, the anti-BCMA binding moiety comprises an antigen binding portion of any of the polypeptides or proteins described herein. The antigen binding portion can be any portion that has at least one antigen binding site. In an embodiment, the anti-BCMA binding moiety is an antibody, a Fab fragment (Fab), F(ab')$_2$ fragment, diabody, triabody, tetrabody, single-chain variable region fragment (scFv), or disulfide-stabilized variable region fragment (dsFv). Preferably, the anti-BCMA binding moiety is a Fab fragment or a dsFv.

In an embodiment, the anti-BCMA binding moiety is an antibody. The antibody may be a monospecific antibody that has antigen specificity for only BCMA or a bispecific antibody having antigen specificity for BCMA and a second antigen other than BCMA. The antibody may be, for example, a recombinant antibody comprising at least one of the inventive polypeptides described herein. As used herein, "recombinant antibody" refers to a recombinant (e.g., genetically engineered) protein comprising at least one of the polypeptides or proteins of the invention and one or more polypeptide chains of an antibody, or a portion thereof. The polypeptide of an antibody, or portion thereof, can be, for example, a constant region of a heavy or light chain, or an Fc fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide or protein of the invention. The polypeptide of an antibody, or portion thereof, can be a polypeptide of any antibody or any antibody fragment.

The antibody of the invention can be any type of immunoglobulin that is known in the art. For instance, the anti-BCMA binding moiety can be an antibody of any isotype, e.g., IgA, IgD, IgE, IgG (e.g., IgG1, IgG2, IgG3, or IgG4), IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for BCMA.

Methods of testing antibodies for the ability to bind to BCMA are known in the art and include any antibody-antigen binding assay, such as, for example, radioimmunoassay (RIA), enzyme-linked immunosorbent assay (ELISA), Western blot, immunoprecipitation, and competitive inhibition assays.

Suitable methods of making antibodies are known in the art and include, for example, standard hybridoma methods, Epstein-Barr virus (EBV)-hybridoma methods, and bacteriophage vector expression systems. Antibodies may be produced in non-human animals.

In a preferred embodiment, the anti-BCMA binding moiety is a single-chain variable region fragment (scFv). A single-chain variable region fragment (scFv) antibody fragment, which is a truncated Fab fragment including the variable (V) domain of an antibody heavy chain linked to a V domain of a light antibody chain via a synthetic peptide, can be generated using routine recombinant DNA technology techniques. Similarly, disulfide-stabilized variable region fragments (dsFv) can be prepared by recombinant DNA technology. The anti-BCMA binding moieties of the invention, however, are not limited to these exemplary types of antibody fragments.

Also, the anti-BCMA binding moiety can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Another embodiment of the invention provides chimeric antigen receptors (CARs) comprising: (a) an antigen binding domain comprising any of the polypeptides, proteins, or anti-BCMA binding moieties described herein, (b) a transmembrane (TM) domain, and (c) an intracellular T cell signaling domain.

A chimeric antigen receptor (CAR) is an artificially constructed hybrid protein or polypeptide containing the antigen binding domains of an antibody (e.g., single chain variable fragment (scFv)) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

The phrases "have antigen specificity" and "elicit antigen-specific response," as used herein, means that the CAR can specifically bind to and immunologically recognize an antigen, such that binding of the CAR to the antigen elicits an immune response.

The CARs of the invention have antigen specificity for BCMA. Without being bound to a particular theory or mechanism, it is believed that by eliciting an antigen-specific response against BCMA, the inventive CARs provide for one or more of the following: targeting and destroying BCMA-expressing cancer cells, reducing or eliminating cancer cells, facilitating infiltration of immune cells to tumor site(s), and enhancing/extending anti-cancer responses.

An embodiment of the invention provides a CAR comprising an antigen binding domain of an anti-BCMA antibody. The antigen binding domain of the anti-BCMA antibody specifically binds to BCMA. The antigen binding domain of the CARs may comprise any of the polypeptides, proteins, or anti-BCMA binding moieties described herein. In an embodiment of the invention, the CAR comprises an anti-BCMA single chain variable fragment (scFv). In this regard, a preferred embodiment of the invention provides a CAR comprising an antigen-binding domain comprising a single chain variable fragment (scFv) that comprises any of the polypeptides or proteins described herein.

In a preferred embodiment of the invention, the CAR comprises a heavy chain and a light chain each of which comprises a variable region comprising a complementarity determining region (CDR) 1, a CDR2, and a CDR3. Preferably, the heavy chain comprises a CDR1 comprising the amino acid sequence of SEQ ID NO: 1 or 7 (CDR1 of heavy chain), a CDR2 comprising the amino acid sequence of SEQ ID NO: 2 or 8 (CDR2 of heavy chain), and a CDR3 comprising the amino acid sequence of SEQ ID NO: 3 or 9 (CDR3 of heavy chain), and the light chain comprises a CDR1 comprising the amino acid sequence of SEQ ID NO: 4 or 10 (CDR1 of light chain), a CDR2 comprising the amino acid sequence of SEQ ID NO: 5 or 11 (CDR2 of light chain), and a CDR3 comprising the amino acid sequence of SEQ ID NO: 6 or 12 (CDR3 of light chain). In this regard, the inventive CAR can comprise the amino acid sequences of (a) SEQ ID NOs: 1-3, (b) SEQ ID NO: 4-6, (c) SEQ ID NO: 1-6, (d) SEQ ID NOs: 7-9, (e) SEQ ID NOs: 10-12, or (f) SEQ ID NOs: 7-12. Preferably the CAR comprises the amino acid sequences of SEQ ID NOs: 1-6 or SEQ ID NO: 7-12.

In an embodiment of the invention, the antigen binding domains of the CARs each comprise a light chain and a heavy chain. The light chain may comprise SEQ ID NO: 14 or 16. The heavy chain may comprise SEQ ID NO: 13 or 15. Accordingly, in an embodiment of the invention, the antigen binding domain comprises the amino acid sequences of (a) SEQ ID NO: 13, (b) SEQ ID NO: 14, (c) SEQ ID NO: 15, (d) SEQ ID NO: 16, (e) SEQ ID NOs: 13 and 14, or (f) SEQ ID NOs: 15 and 16. Preferably, the CAR comprises the amino acid sequences of (i) SEQ ID NOs: 13-14 or (ii) SEQ ID NOs: 15-16.

In an embodiment, the antigen binding domain of the CAR comprises a leader sequence. In an embodiment of the invention, while the leader sequence may facilitate expression of the CAR on the surface of the cell, the presence of the leader sequence in an expressed CAR is not necessary in order for the CAR to function. In an embodiment of the invention, upon expression of the CAR on the cell surface, the leader sequence may be cleaved off of the CAR. Accordingly, in an embodiment of the invention, the CAR lacks a leader sequence.

In an embodiment, the CAR comprises an immunoglobulin constant domain. Preferably, the immunoglobulin domain is a human immunoglobulin sequence. In an embodiment, the immunoglobulin constant domain comprises an immunoglobulin CH2 and CH3 immunoglobulin G (IgG1) domain sequence (CH2CH3). Without being bound to a particular theory, it is believed that the CH2CH3 domain extends the binding motif of the scFv away from the membrane of the CAR-expressing cells and may more accurately mimic the size and domain structure of a native TCR. In some embodiments, the CAR may lack an immunoglobulin constant domain.

In an embodiment of the invention, the CAR comprises a TM domain. In an embodiment of the invention, the TM domain comprises the TM domain of CD8 or CD28. In a preferred embodiment, the CD8 and CD28 are human.

In an embodiment of the invention, the CAR comprises an intracellular T cell signaling domain comprising the intracellular T cell signaling domain of one or more of i) CD28, ii) CD137, and iii) CD3 zeta (t). In a preferred embodiment, the CD28, CD137, and CD3 zeta are human. CD28 is a T cell marker important in T cell co-stimulation. CD137, also known as 4-1BB, transmits a potent costimulatory signal to T cells, promoting differentiation and enhancing long-term survival of T lymphocytes. CD3t associates with TCRs to produce a signal and contains immunoreceptor tyrosine-based activation motifs (ITAMs).

In an embodiment of the invention, the CAR comprises a TM domain comprising the TM domain of CD28 and an intracellular T cell signaling domain comprising the intracellular T cell signaling domains of CD28 and CD3 zeta.

In an embodiment of the invention, the CAR comprises a TM domain comprising the TM domain of CD8 and an intracellular T cell signaling domain comprising the intracellular T cell signaling domains of CD28, CD137, and CD3 zeta.

In an embodiment of the invention, the CAR comprises a TM domain comprising the TM domain of CD8 and an intracellular T cell signaling domain comprising the intracellular T cell signaling domains of CD137 and CD3 zeta.

Included in the scope of the invention are functional portions of the inventive polypeptides, proteins, and CARs described herein. The term "functional portion," when used in reference to a polypeptide, protein, or CAR, refers to any part or fragment of the polypeptide, protein, or CAR of the invention, which part or fragment retains the biological activity of the polypeptide, protein, or CAR of which it is a part (the parent polypeptide, protein, or CAR). Functional portions encompass, for example, those parts of a polypeptide, protein, or CAR that retain the ability to recognize target cells, or detect, treat, or prevent cancer, to a similar extent, the same extent, or to a higher extent, as the parent polypeptide, protein, or CAR. In reference to the parent polypeptide, protein, or CAR, the functional portion can comprise, for instance, about 10%, 25%, 30%, 50%, 68%, 80%, 90%, 95%, or more, of the parent polypeptide, protein, or CAR.

The functional portion can comprise additional amino acids at the amino or carboxy terminus of the portion, or at both termini, which additional amino acids are not found in the amino acid sequence of the parent polypeptide, protein, or CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent polypeptide, protein, or CAR.

Included in the scope of the invention are functional variants of the inventive polypeptides, proteins, or CARs described herein. The teini "functional variant," as used herein, refers to a polypeptide, protein, or CAR having substantial or significant sequence identity or similarity to a parent polypeptide, protein, or CAR, which functional variant retains the biological activity of the polypeptide, protein, or CAR of which it is a variant. Functional variants encompass, for example, those variants of the polypeptide, protein, or CAR described herein (the parent polypeptide, protein, or CAR) that retain the ability to recognize target cells to a similar extent, the same extent, or to a higher extent, as the parent polypeptide, protein, or CAR. In reference to the parent polypeptide, protein, or CAR, the functional variant can, for instance, be at least about 30%, about 50%, about 75%, about 80%, about 85%, about 90%, about 91%, about 92%, about 93%, about 94%, about 95%, about 96%, about 97%, about 98%, about 99% or more identical in amino acid sequence to the parent polypeptide, protein, or CAR.

A functional variant can, for example, comprise the amino acid sequence of the parent polypeptide, protein, or CAR with at least one conservative amino acid substitution. Alternatively or additionally, the functional variants can comprise the amino acid sequence of the parent polypeptide, protein, or CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent polypeptide, protein, or CAR.

Amino acid substitutions of the inventive polypeptides, proteins, or CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The polypeptide, protein, or CAR can consist essentially of the specified amino acid sequence or sequences described herein, such that other components, e.g., other amino acids, do not materially change the biological activity of the polypeptide, protein, CAR, functional portion, or functional variant.

The polypeptides, proteins, or CARs of embodiments of the invention (including functional portions and functional variants) can be of any length, i.e., can comprise any number of amino acids, provided that the polypeptides, proteins, or CARs (or functional portions or functional variants thereof) retain their biological activity, e.g., the ability to specifically bind to antigen, detect diseased cells in a mammal, or treat or prevent disease in a mammal, etc. For example, the polypeptide, protein, or CAR can be about 50 to about 5000 amino acids long, such as 50, 70, 75, 100, 125, 150, 175, 200, 300, 400, 500, 600, 700, 800, 900, 1000 or more amino acids in length.

The polypeptides, proteins, or CARs of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The polypeptides, proteins, or CARs of embodiments of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized.

The polypeptides, proteins, or CARs of embodiments of the invention (including functional portions and functional variants thereof) can be obtained by methods known in the art. The polypeptides, proteins, or CARs may be made by any suitable method of making polypeptides or proteins. Suitable methods of de novo synthesizing polypeptides and proteins are known in the art. Also, polypeptides and proteins can be recombinantly produced using nucleic acids and standard recombinant methods. Further, some of the polypeptides, proteins, or CARs of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the polypeptides, proteins, or CARs described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive polypeptides, proteins, or CARs can be synthetic, recombinant, isolated, and/or purified.

Included in the scope of the invention are conjugates, e.g., bioconjugates, comprising any of the inventive polypeptides, proteins, CARs, anti-BCMA binding moieties, or functional portions or functional variants thereof. In this regard, an embodiment of the invention provides a conjugate comprising (a) any of the polypeptides, proteins, CARs, or anti-BCMA binding moieties described herein conjugated or fused to (b) an effector molecule. The effector molecule may be any therapeutic molecule or a molecule that facilitates the detection of the conjugate. The effector molecule is not limited and may be any suitable effector molecule. For example, the effector molecule may be any one or more of a drug, toxin, label (e.g., any of the detectable labels described herein), small molecule, or another antibody. For example, the toxin may be (i) *Pseudomonas* exotoxin A ("PE"), (ii) a cytotoxic fragment of PE (e.g., domain III of PE) or (iii) a cytotoxic variant of (i) or (ii) such as, e.g., any of PE-LR, PE-LO10R456A, PE-T20, PE-T20-KDEL, PE4E, PE40, PE38, PE24, PE25, PE38QQR, PE38KDEL, and PE35, as described in, e.g., U.S. Pat. Nos. 4,892,827; 5,512,658; 5,602,095; 5,608,039; 5,821,238; 5,854,044; 8,871,906; 8,907,060; 8,936,792; 9,346,859; 9,206,240; and 9,388,222, each of which is incorporated herein by reference. Examples of drugs that may be suitable in the inventive conjugates include, but are not limited to, pyrrolobenzodiazepine (PBD) dimer, tubulin-binders such as, for example, dolastatin 10, monomethyl dolastatin 10, auristain E, monomethyl auristatin E (MMAE), auristatin F, monomethyl auristatin F, HTI-286, tubulysin M, maytansinoid AP-3, cryptophycin, Boc-Val-Dil-Dap-OH, tubulysin IM-1, Boc-Val-Dil-Dap-Phe-OMe, tubulysin IM-2, Boc-Nme-Val-Val-Dil-Dap-OH, tubulysin IM-3, and colchicine DA; DNA-alkylators (duocarmycin analogs) such as, for example, duocarmycin SA, duocarmycin CN, duocarmycin DMG, duocarmycin DMA, duocarmycin MA, duocarmycin TM, duocarmycin MB, duocarmycin GA; tomaymycin DM; SJG-136; illudin S; irofulven; apaziquone; triptolide; staurosporine; camptothecin; methotrexate; and other anti-cancer drugs such as, for example, kinase inhibitors, histone deacetylase (HDAC) inhibitors, proteasome inhibitors, and matrix metalloproteinase (MMP) inhibitors.

The polypeptides, proteins, CARs, or anti-BCMA binding moieties described herein may be conjugated or fused to (b) an effector molecule directly or indirectly, e.g., via a linker. The linker may be any suitable linker known in the art. In an embodiment, the linker is a cleavable linker that may be cleaved upon administration of the conjugate to a mammal. Examples of linkers that may be suitable for use in the inventive conjugates include, but are not limited to, any of the linkers described herein with respect to other aspects of the invention.

Further provided by an embodiment of the invention is a nucleic acid comprising a nucleotide sequence encoding any of the polypeptides, proteins, CARs, anti-BCMA binding moieties, conjugates, or functional portions or functional variants thereof. The nucleic acids of the invention may comprise a nucleotide sequence encoding any of the linkers, antigen binding domains, immunoglobulin domains, TM domains, and/or intracellular T cell signaling domains described herein.

An embodiment of the invention provides a nucleic acid comprising a nucleotide sequence encoding any of the polypeptides, proteins, or anti-BCMA binding moieties described herein. In this regard, the nucleic acid comprises a nucleotide sequence encoding (i) first and second variable regions SEQ ID NOs: 13 and 14, respectively, or (ii) first and second variable regions SEQ ID NOs: 15 and 16, respectively. Another embodiment of the invention provides a nucleic acid comprising a nucleotide sequence encoding any of the CDR regions described herein. In this regard, the nucleic acid comprises a nucleotide sequence encoding the amino acid sequences of SEQ ID NOs: (a) 1-3, (b) SEQ ID NOs: 4-6, (c) SEQ ID NOs: 7-9, (d) SEQ ID NOs: 10-12, (e) SEQ ID NOs: 1-6, or (f) SEQ ID NOs: 7-12. Another embodiment of the invention provides a nucleic acid comprising a nucleotide sequence encoding any of the CARs described herein.

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions. In some embodiments, the nucleic acid may encode additional amino acid sequences that do not affect the function of the polypeptide, protein, or CAR and which may or may not be translated upon expression of the nucleic acid by a host cell (e.g., AAA). In an embodiment of the invention, the nucleic acid is complementary DNA (cDNA). In an embodiment of the invention, the nucleic acid comprises a codon-optimized nucleotide sequence.

The nucleic acids of an embodiment of the invention may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can consist essentially of the specified nucleotide sequence or sequences described herein, such that other components, e.g., other nucleotides, do not materially change the biological activity of the encoded CAR, polypeptide, protein, anti BCMA-binding moieties, functional portion, or functional variant.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Green and Sambrook, *Molecular Cloning: A Laboratory Manual*, Cold Spring Harbor Laboratory Press, 4th Ed. (2012). The nucleic acids can be constructed based on chemical synthesis and/or enzymatic ligation reactions using procedures known in the art. See, for example, Green et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetyl cytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any isolated or purified nucleotide sequence which encodes any of the polypeptides, proteins, CARs, anti-BCMA binding moieties, conjugates, or functional portions or functional variants thereof. Alternatively, the nucleotide sequence can comprise a nucleotide sequence which is degenerate to any of the sequences or a combination of degenerate sequences.

An embodiment of the invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive polypeptides, proteins, CARs, anti-BCMA binding moieties, conjugates, or functional portions or functional variants thereof. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids of the invention can be incorporated into a recombinant expression vector. In this regard, an embodiment of the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). The recombinant expression vector may be a viral vector, e.g., a retroviral vector.

A number of transfection techniques are generally known in the art. Transfection methods include calcium phosphate co-precipitation, direct micro injection into cultured cells, electroporation, liposome mediated gene transfer, lipid mediated transduction, and nucleic acid delivery using high velocity microprojectiles.

In an embodiment, the recombinant expression vectors of the invention can be prepared using standard recombinant DNA techniques described in, for example, Green, supra. Constructs of expression vectors, which are circular or linear, can be prepared to contain a replication system functional in a prokaryotic or eukaryotic host cell. Replication systems can be derived, e.g., from ColE1, 2μ plasmid, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the polypeptides, proteins, CARs, anti-BCMA binding moieties, conjugates, or functional portions or functional variants thereof, or to the nucleotide sequence which is complementary to or which hybridizes to the nucleotide sequence encoding the inventive polypeptides, proteins, CARs, anti-BCMA binding moieties, conjugates, or functional portions or functional variants thereof. The selection of promoters, e.g., strong, weak, inducible, tissue-specific and developmental-specific, is within the ordinary skill of the artisan. Similarly, the combining of a nucleotide sequence with a promoter is also within the ordinary skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine daminase, purine nucleoside phosphorylase, and nitroreductase.

An embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a E. coli cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant polypeptide, protein, CAR, anti-BCMA binding moiety, conjugate, or functional portion or functional variant thereof, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a B cell or a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4$^+$/CD8$^+$ double positive T cells, CD4$^+$ helper T cells, e.g., Th$_1$ and Th$_2$ cells, CD8$^+$ T cells (e.g., cytotoxic T cells), tumor infiltrating cells, memory T cells, naïve T cells, and the like. The T cell may be a CD8$^+$ T cell or a CD4$^+$ T cell.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

The polypeptides, proteins, CARs (including functional portions and variants thereof), nucleic acids, recombinant expression vectors, host cells (including populations thereof), anti-BCMA binding moieties, and conjugates, all of which are collectively referred to as "inventive anti-BCMA materials" hereinafter, can be isolated and/or purified. The term "isolated" as used herein means having been removed from its natural environment. The term "purified" or "isolated" does not require absolute purity or isolation; rather, it is intended as a relative term. Thus, for example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example, at least about 70%, of the total cell content of the preparation. For example, the purity can be at least about 50%, can be greater than about 60%, about 70% or about 80%, or can be about 100%.

The inventive anti-BCMA materials can be formulated into a composition, such as a pharmaceutical composition. In this regard, an embodiment of the invention provides a pharmaceutical composition comprising any of the inventive anti-BCMA materials described herein and a pharmaceutically acceptable carrier. The inventive pharmaceutical compositions containing any of the inventive anti-BCMA materials can comprise more than one inventive anti-BCMA material, e.g., a conjugate and a nucleic acid, or two or more different conjugates Alternatively, the pharmaceutical composition can comprise an inventive anti-BCMA material in combination with other pharmaceutically active agents or drugs, such as chemotherapeutic agents, e.g., asparaginase, bortezomib (e.g., VELCADE bortezomib), busulfan, carboplatin, cisplatin, daunorubicin, dexamethasone, doxorubicin, fluorouracil, gemcitabine, hydroxyurea, lenalidomide, melphalan, methotrexate, paclitaxel (e.g., ABRAXANE paclitaxel), rituximab, vinblastine, vincristine, etc. In a preferred embodiment, the pharmaceutical composition comprises the inventive conjugate. Preferably, the other pharmaceutically active agent or drug is melphalan, bortezomib, lenalidomide, dexamethasone, or paclitaxel.

The inventive anti-BCMA materials can be provided in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

With respect to pharmaceutical compositions, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive anti-BCMA material, as well as by the particular method used to administer the inventive anti-BCMA material. Accordingly, there are a variety of suitable formulations of the pharmaceutical composition of the invention. Preservatives may be used. Suitable preservatives may include, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition.

Suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

The concentration of inventive anti-BCMA material in the pharmaceutical formulations can vary, e.g., from less than about 1%, usually at or at least about 10%, to as much as, for example, about 20% to about 50% or more by weight, and can be selected primarily by fluid volumes, and viscosities, in accordance with the particular mode of administration selected.

Methods for preparing administrable (e.g., parenterally administrable) compositions are known or apparent to those skilled in the art and are described in more detail in, for example, *Remington: The Science and Practice of Pharmacy*, Pharmaceutical Press; 22nd Ed. (2012).

The following formulations for oral, aerosol, parenteral (e.g., subcutaneous, intravenous, intraarterial, intramuscular, intradermal, interperitoneal, and intrathecal), and topical administration are merely exemplary and are in no way limiting. More than one route can be used to administer the inventive anti-BCMA materials, and in certain instances, a particular route can provide a more immediate and more effective response than another route.

Formulations suitable for oral administration can comprise or consist of (a) liquid solutions, such as an effective amount of the inventive anti-BCMA material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard or softshelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive anti-BCMA material in a flavor, usually sucrose and acacia or tragacanth, as well as pastilles comprising the inventive anti-BCMA material in an inert base, such as gelatin and glycerin, or sucrose and acacia, emulsions, gels, and the like containing, in addition to, such excipients as are known in the art.

Formulations suitable for parenteral administration include aqueous and nonaqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive anti-BCMA material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral fonnulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain, for example, from about 0.5% to about 25% by weight of the inventive anti-BCMA material in solution. Preservatives and buffers may be used. In order to minimize or eliminate irritation at the site of injection, such compositions may contain one or more nonionic surfactants having, for example, a hydrophile-lipophile balance (HLB) of from about 12 to about 17. The quantity of surfactant in such formulations will typically range, for example, from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use.

Extemporaneous injection solutions and suspensions can be prepared from sterile powders, granules, and tablets of the kind previously described.

Injectable formulations are in accordance with an embodiment of the invention. The requirements for effective pharmaceutical carriers for injectable compositions are well-known to those of ordinary skill in the art (see, e.g., *A Practical Guide to Contemporary Pharmacy Practice*, 3rd Edition, Lippincott Williams and Wilkins, Philadelphia, Pa., Thompson and Davidow, eds., (2009), and *Handbook on Injectable Drugs*, Trissel, 16th ed., (2010)).

Topical formulations, including those that are useful for transdermal drug release, are well known to those of skill in the art and are suitable in the context of embodiments of the invention for application to skin. The inventive anti-BCMA material, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

An "effective amount" or "an amount effective to treat" refers to a dose that is adequate to prevent or treat cancer in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the active selected, method of administration, timing and frequency of administration, the existence, nature, and extent of any adverse side-effects that might accompany the administration of a particular active, and the desired physiological effect. It will be appreciated by one of skill in the art that various diseases or disorders could require prolonged treatment involving multiple administrations, perhaps using the inventive anti-BCMA materials in each or various rounds of administration. By way of example and not intending to limit the invention, the dose of the inventive anti-BCMA material can be about 0.001 to about 1000 mg/kg body weight of the subject being treated/day, from about 0.01 to about 10 mg/kg body weight/day, about 0.01 mg to about 1 mg/kg body weight/day.

For purposes of the invention, the amount or dose of the inventive anti-BCMA material administered should be sufficient to effect a therapeutic or prophylactic response in the subject or animal over a reasonable time frame. For example, the dose of the inventive anti-BCMA material should be sufficient to bind to antigen or detect, treat or prevent disease in a period of from about 2 hours or longer, e.g., about 12 to about 24 or more hours, from the time of administration. In certain embodiments, the time period could be even longer. The dose will be determined by the efficacy of the particular inventive anti-BCMA material and the condition of the animal (e.g., human), as well as the body weight of the animal (e.g., human) to be treated.

For purposes of the invention, an assay, which comprises, for example, comparing the extent to which target cells are killed upon administration of a given dose of the inventive anti-BCMA material to a mammal, among a set of mammals of which is each given a different dose of the inventive anti-BCMA material, could be used to determine a starting dose to be administered to a mammal. The extent to which target cells are killed upon administration of a certain dose can be assayed by methods known in the art.

In addition to the aforedescribed pharmaceutical compositions, the inventive anti-BCMA materials can be formulated as inclusion complexes, such as cyclodextrin inclusion complexes, or liposomes. Liposomes can serve to target the inventive anti-BCMA materials to a particular tissue. Liposomes also can be used to increase the half-life of the inventive anti-BCMA materials. Many methods are available for preparing liposomes.

The delivery systems useful in the context of embodiments of the invention may include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix and (b) diffusional systems in which an active component permeates at a controlled rate from a polymer. In addition, pump-based hardware delivery systems can be used, some of which are adapted for implantation.

One of ordinary skill in the art will readily appreciate that the inventive anti-BCMA materials of the invention can be modified in any number of ways, such that the therapeutic or prophylactic efficacy of the inventive anti-BCMA materials is increased through the modification. For instance, the inventive anti-BCMA materials can be modified into a depot form, such that the manner in which the inventive anti-BCMA materials is released into the body to which it is administered is controlled with respect to time and location within the body. Depot forms of inventive anti-BCMA materials can be, for example, an implantable composition comprising the inventive anti-BCMA materials and a porous or non-porous material, such as a polymer, wherein the inventive anti-BCMA materials are encapsulated by or diffused throughout the material and/or degradation of the non-porous material. The depot is then implanted into the desired location within the body and the inventive anti-BCMA materials are released from the implant at a predetermined rate.

When the inventive anti-BCMA materials are administered with one or more additional therapeutic agents, one or more additional therapeutic agents can be coadministered to the mammal. By "coadministering" is meant administering one or more additional therapeutic agents and the inventive anti-BCMA materials sufficiently close in time such that the inventive anti-BCMA materials can enhance the effect of one or more additional therapeutic agents, or vice versa. In this regard, the inventive anti-BCMA materials can be administered first and the one or more additional therapeutic agents can be administered second, or vice versa. Alternatively, the inventive anti-BCMA materials and the one or more additional therapeutic agents can be administered simultaneously. Exemplary therapeutic agents that can be co-administered with the anti-BCMA materials include the chemotherapeutic agents described herein with respect to other aspects of the invention. For purposes of the inventive methods, wherein host cells or populations of cells are administered to the mammal, the cells can be cells that are allogeneic or autologous to the mammal.

It is contemplated that the inventive anti-BCMA materials and pharmaceutical compositions can be used in methods of treating or preventing cancer in a mammal. Without being bound to a particular theory or mechanism, the inventive anti-BCMA materials have biological activity, e.g., ability to recognize antigen, e.g., BCMA, such that the anti-BCMA material, can direct an effector molecule to a target cell or target tissue. In this regard, an embodiment of the invention provides a method of treating or preventing cancer in a mammal comprising administering to the mammal any of the polypeptides, proteins, CARs, functional portions, functional variants, nucleic acids, recombinant expression vectors, host cells, population of cells, anti-BCMA binding moieties, conjugates, and/or the pharmaceutical compositions of the invention in an amount effective to treat or prevent cancer in the mammal.

An embodiment of the invention further comprises lymphodepleting the mammal prior to administering the inventive anti-BCMA material(s). Examples of lymphodepletion include, but may not be limited to, nonmyeloablative lymphodepleting chemotherapy, myeloablative lymphodepleting chemotherapy, total body irradiation, etc.

For purposes of the inventive methods, wherein host cells or populations of cells are administered, the cells can be cells that are allogeneic or autologous to the mammal. Preferably, the cells are autologous to the mammal.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the inventive methods, the cancer can be any cancer, including any of acute lymphocytic cancer, acute myeloid leukemia, rhabdomyosarcoma, bladder cancer (e.g., bladder carcinoma), bone cancer, brain cancer (e.g., medulloblastoma, neuroblastoma, and glioblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, DLBCL lymphoma, Ewing's sarcoma, esophageal cancer, cervical cancer, fibrosarcoma, gastrointestinal carcinoid tumor, head and neck cancer (e.g., head and neck squamous cell carcinoma), Hodgkin's lymphoma, hypopharynx cancer, kidney cancer, larynx cancer, leukemia, liquid tumors, liver cancer, lung cancer (e.g., non-small cell lung carcinoma), lymphoma, malignant mesothelioma, mastocytoma, melanoma, multiple myeloma, nasopharynx cancer, neuroblastoma, non-Hodgkin lymphoma, B-chronic lymphocytic leukemia, hairy cell leukemia, acute lymphocytic leukemia (ALL) lymphoma, and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, and ureter cancer. Preferably, the cancer is Burkitt's lymphoma, DLBCL lymphoma, ALL lymphoma, Hodgkin's lymphoma or multiple myeloma. In an embodiment, the cancer is characterized by the expression or overexpression of BCMA.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the cancer, or a symptom or condition thereof, or delaying or preventing recurrence of the cancer.

Another embodiment of the invention provides a use of any of the polypeptides, proteins, CARs, functional portions, functional variants, nucleic acids, recombinant expression vectors, host cells, population of cells, anti-BCMA binding moieties, conjugates, or pharmaceutical compositions of the invention for the treatment or prevention of cancer in a mammal.

Another embodiment of the invention provides a method of detecting the presence of cancer in a mammal, comprising: (a) contacting a sample comprising one or more cells from the mammal with any of the polypeptides, proteins, CARs, functional portions, functional variants, nucleic acids, recombinant expression vectors, host cells, population of cells, anti-BCMA binding moieties, or conjugates of the invention, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the inventive method of detecting the presence of cancer in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

For purposes of the inventive detecting method, the contacting can take place in vitro or in vivo with respect to the mammal. Preferably, the contacting is in vitro.

Also, detection of the complex can occur through any number of ways known in the art. For instance, the inventive CARs, polypeptides, proteins, functional portions, functional variants, nucleic acids, recombinant expression vectors, host cells, populations of cells, anti-BCMA binding moieties, or conjugates, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The following examples further illustrate the invention but, of course, should not be construed as in any way limiting its scope.

EXAMPLES

The following materials and methods were employed in the experiments described in Examples 1-11.

Plasmids

BCMA (TNFRSF17) cDNA was cloned and a pair of expression vectors was constructed. One vector encoded the full-length human BCMA and the other encoded the extracellular domain of human BCMA (residues 1-54) fused to the Fc region (CH2 and CH3 domains) of the rabbit IgG heavy chain and the hinge region. First, the full-length cDNA of human BCMA was cloned into pcDNA6 (Invitrogen, Carlsbad, Calif.), a mammalian expression vector under the control of cytomegalovirus promotor, generating pcDNA6/BCMA. For the Fc-fusion proteins, DNA fragments encoding the extracellular domain of human BCMA were amplified by PCR and digested by EcoRI and BglII and cloned into the pFUSE-rFcI expression vector (InvivoGen, San Diego, Calif.), generating pFUSE/BCMA-rFc.

Cells 293T cells were grown in DMEM supplemented with 10% fetal bovine serum (FBS). P3U1 myeloma cells were used as the fusion partner for hybridoma formation and maintained in Iscove's Modified Dulbecco's Medium (IMDM, Invitrogen) with 15% fetal bovine serum (FBS).

Production of Recombinant BCMA-rFc Fusion Proteins

To establish stable cell lines expressing BCMA-rFc fusion protein, 293T cells were transfected with pFUSE/BCMA-rFc by LIPOFECTAMINE LTX with PLUS reagent (Invitrogen) according to the manufacturer's instructions. Transfected cells were selected in culture medium containing 200 mg/ml ZEOCIN antibiotic (Invitrogen) by several rounds of limiting dilution. A stable cell line with the highest BCMA-rFc expression was used for large-scale production in a CELLINE AD 1000 (Wheaton, Millville, N.J.) two-compartment bioreactor facilitating a high cell density. The BCMA-rFc fusion protein was purified with a protein G-SEPAHROSE column (GE healthcare, Pittsburgh, Pa.).

Immunization

Female BALB/c mice (6 weeks old) were immunized with 25 μg of recombinant BCMA-rFc fusion protein in TITERMAX Gold Adjuvant liquid (Sigma-Aldrich, St Louis, Mo.) intraperitoneally for the first immunization, and subsequently immunized 5 times with BCMA-rFc without adjuvant. The titer of antibody from mouse serum was tested before the cell fusion. To boost BCMA-immunized mice, 100 μg of BCMA-rFc with adjuvant were injected into mice intraperitoneally. Spleens were harvested 72 hours (h) after the final boost for cell fusion. All animals were maintained in accordance with institutional guidelines.

Cell Fusion and Hybridoma Culture

Splenocytes and P3U1 cells were washed three times and twice, respectively, with serum-free IMDM. The splenocytes were counted and mixed with P3U1 at a 4:1 ratio. The mixed cells were centrifuged and the cell pellet was resuspended in 1 ml of 40% Polyethylene glycol (PEG4000, EMD Millipore, Billerica, Mass.) that was added drop by drop over a 1-min period with swirling. After swirling for an additional 1 min, the suspension was slowly diluted with pre-warmed (37 C) IMDM. The resulting suspension was centrifuged and the cell pellet was resuspended at $2.5 \times 10^6$/ml in IMDM supplemented with 20% of FBS, 1 mM sodium pyruvate, 2 mM L-glutamine, 50 μM 2-mercaptoethanol, 10 μg/ml gentamycin, 8 μg/ml bovine insulin, 1 μg/ml bovine transferrin, 1 U/ml of human IL-6. The cell suspension was seeded in 96-well pates at $2.5 \times 10^5$ cells/well and cultured in $CO_2$ incubator. On the day after fusion, 100 μl of fresh HAT medium was added. On days 4 and 7, half of the spent medium was replaced by fresh HAT medium. Antibody production in culture supernatants was assayed on day 10 or 11 by fluorescence activated cell sorter (FACS) screening as described below.

FACS Screening

For transfection experiments, 293T cells were seeded in 100 mm dishes (BD Biosciences, Bedford, Mass.) and grown at the subconfluent densities. pcDNA6/BCMA, pcDNA/TACI, or pcDNA6/BAFFR (6 μs) were transfected per dish by LIPOFECTAMINE LX and PLUS reagent according to the manufacturer's instructions. After 24 h, the transiently transfected cells were harvested and used for FACS screening. Cells ($1-5 \times 10^5$) were incubated with serial dilution of hybridoma supernatants in FACS buffer (PBS containing 5% FBS and 0.1% sodium azide) for 1 h on ice. After washing twice with FACS buffer, the cells were incubated with 1:200 dilution of R-Phycoerythrin (PE)-labelled goat anti-mouse IgG F(ab')2 (Jackson Immuno Research Laboratories, West Grove, Pa.) for 30 min. After washing twice, the cells were resuspended in 180 μl FACS buffer containing 10 nM TO-PRO-3 stain (Invitrogen), and the fluorescence associated with the live cells was measured using a BD ACCURI C6 flow cytometer (BD Biosciences). Positive hybridoma clones were transferred to 24-well pates. To exclude the false positive in the first screening, 24-well culture supernatants were re-assayed 2 days after transfer. The specific hybridomas were cloned by several rounds of limiting dilution and grown in a CELLINE flask to harvest the MAbs in the culture supernatant. The isotype of established monoclonal antibodies (MAb) was determined by a mouse MAb isotyping reagents (Sigma-Aldrich). Immunoglobulin concentrations in the culture supernatants were determined by a sandwich ELISA.

ELISA

MAXISORP 96-well ELISA plates (Nalge Nunc, Rochester, N.Y.) were coated with 100 ng/well of goat anti-rabbit IgG (Jackson Immuno Research Laboratories) in PBS overnight at 4° C. After blocking, 5 ng/well of BCMA-rFc, TACI-rFC, or BAFFR-rFc were added to the plates and incubated for 2 h at room temperature. After washing, 4 μg/ml of hybridoma supernatants were added to the plates and incubated for 2 h at room temperature. After washing, the bound MAbs were detected by a 1 h incubation with alkaline phosphatase (ALP)-labelled goat anti-mouse IgG (Jackson Immuno Research Laboratories) followed by p-nitrophenyl phosphate (pNPP, Fisher Scientific, Pittsburgh, Pa.).

Affinity Determination

The binding kinetics of MAbs to BCMA were measured by bio-layer interferometry using a BLITZ (ForteBio, Menlo Park, Calif.) instrument. According to the manufacturer's instructions, BCMA-rFc were immobilized on amine-reactive second-generation biosensors by amine coupling following the activation of the sensor surface with N-hydroxysuccinimide (NHS) and N-ethyl-N-(3-dimethylaminopropyl) carbodiimide hydrochloride (EDC). Serial dilutions of MAbs were run across sensor surface at five different concentration in PBS (pH 7.4). The sensorgram data set was globally fit using the built-in BLITZ software to determine association rate constant ($K_a$), dissociation rate constant (Kd), and affinity constant ($K_D$).

Example 1

This example demonstrates the production of hybridomas secreting anti-BCMA mAbs.

Mice were intraperitoneally immunized with BCMA-rFc fusion protein in adjuvant for the first immunization, and subsequently immunized 5 times with BCMA-rFc without adjuvant. High antibody titers (1:10,000) against the BCMA-expressing 293T cells were detected in the sera from mice immunized with BCMA-rFc. The mice with high-titer were given a final boost by injecting intraperitoneally BCMA-rFc with adjuvant, and 3 days later, the spleens were fused with P3U1 myeloma. The culture supernatants of hybridomas were screened for the production of specific mAbs by FACS analysis. After FACS screening, eleven positive clones were selected. Among 11 clones, BM303 showed the highest affinity to the native conformation of BCMA. The isotyping test revealed that all of the selected mAbs were IgG1 with a κ light chain.

Example 2

This example demonstrates that BM24 and BM306 antibodies specifically bind to BCMA.

To examine the cross-reactivity of the anti-BCMA mAbs with other TNFR superfamily members, the reactivity of each mAb at a saturated concentration (4 µg/ml) to native TNFRs (BCMA, TACI or BAFFR) expressed by transfected 293T cells was tested by FACS. The reactivity of each mAb to the TNFR-rFc fusion proteins was tested by ELISA. These results indicated that 5 mAbs (BM101, BM226, BM303, BM309 and BM313) exhibited cross-reactivity in varying degrees with TACI, whereas the binding of each of BM14, BM24, BM201, BM219, BM222 and BM306 was specific to BCMA in both assays.

Example 3

This example demonstrates the binding kinetics of BM24 and BM306.

BM24 and BM306 selectively bind to BCMA antigen on the cell surface with high affinity and specificity. The binding kinetics of these two anti-BCMA mAbs against BCMA-rFc protein were measured by bio-layer interferometry. Serial dilutions of anti-BCMA MAbs (20, 10, 5, 2.5, 1.25 µg/ml) were applied to the BCMA-rFc immobilized sensor and detected. Real-time biomolecular interaction analyses were performed with BLITZ software. The results are shown in Table 1. BM306 showed a high association rate constant ($K_a$) compared to BM24. The dissociation constants ($K_D$) of both mAbs were less than $1 \times 10^{-12}$ (exceeded the detection limits).

TABLE 1

| Sample | $K_D$ (M) | $k_a$ (1/Ms) | $k_d$ (1/s) |
|---|---|---|---|
| BM24 | $<1 \times 10^{-12}$ | $2.97 \times 10^5$ | $<1 \times 10^{-7}$ |
| BM306 | $<1 \times 10^{-12}$ | $4.15 \times 10^5$ | $<1 \times 10^{-7}$ |

Example 4

This example demonstrates the cloning of the Fv fragments from BM24 and BM306 hybridomas.

Both of the BM24 and BM306 mAbs are of the IgG1 isotype. The heavy and light chains were cloned from the BM24 and BM306-expressing hybridomas using IgG1 isotype-specific oligo primers. The SEQ ID NOs for the amino acid sequences are shown in Table 2.

TABLE 2

| BM24 VH | SEQ ID NO: 13 |
| BM24 VL | SEQ ID NO: 14 |
| BM306 VH | SEQ ID NO: 15 |
| BM306 VL | SEQ ID NO: 16 |

Example 5

This example demonstrates the development of PE-based immunotoxins using Fvs from BM24 and BM306.

Immunotoxins were prepared in which either a Fab or dsFv fragment was connected to variants of domain III of PE. The resulting anti-BCMA immunotoxins are listed below:

LMB34: BM24-Fab-LO10R456A;

LMB38: BM24-Fab-LR-GGS;

LMB63: BM24-Fab-LR-GGS-T20;

LMB64: BM24-Fab-LR-GGS-T20-KDEL;

LMB70: BM306-Fab-LR-GGS;

LMB75: BM306-dsFv-LR-GGS;

LMB92: BM306-Fab-LO10R456A;

LMB94: BM306-dsFv-GGSx4-PE24 (no furin site);

LMB103: BM306-Fab-LR-GGS-T20; and

LMB107: BM306-dsFv-PE38.

Example 6

This example demonstrates the activity of anti-BCMA immunotoxins (IT) against cell lines.

The activity of the anti-BCMA immunotoxins against BCMA-expressing cell lines and cells from four multiple myeloma patients was tested by WST assay. The $IC_{50}$ value for each immunotoxin is summarized in Table 3. LMB38 and LMB70 with wild type PE24-GGS was the most active IT against the BCMA-expressing H929 cell line with an $IC_{50}$ of 1.0-1.5 ng/ml.

TABLE 3

| | $IC_{50}$ (ng/ml) | | | | | | | | | | |
|---|---|---|---|---|---|---|---|---|---|---|---|
| | LMB34 | LMB38 | LMB63 | LMB64 | LMB70 | LMB75 | LMB92 | LMB94 | LMB103 | LMB107 | BM306 |
| Cell line | | | | | | | | | | | |
| U266B | 8.0 | 1.9 | NT | NT | 5.0 | NT | 16.0 | NT | NT | NT | >1000 |
| H929 | 3.6 | 1.2 | 7.0 | 8.0 | 1.1 | 1.3 | 3.1 | 50.0 | 6.0 | 1.1 | >1000 |

TABLE 3-continued

|  | LMB34 | LMB38 | LMB63 | LMB64 | IC$_{50}$ (ng/ml) LMB70 | LMB75 | LMB92 | LMB94 | LMB103 | LMB107 | BM306 |
|---|---|---|---|---|---|---|---|---|---|---|---|
| RPMI-8226 | 20.0 | 6.9 | NT | NT | 5.1 | NT | 18.0 | NT | NT | NT | >1000 |
| LP-1 | 40.0 | 25.0 | NT | NT | 20.0 | NT | 36.0 | NT | NT | NT | NT |
| JJN-3 | 9.0 | 2.5 | NT | NT | 4.0 | NT | 10.0 | NT | NT | NT | >1000 |
| KMS-18 | 52.0 | 55.0 | NT | NT | 65.0 | NT | 59.0 | NT | NT | NT | NT |
| Jeko-1 | >100 | >100 | NT | NT | >100 | NT | >100 | NT | NT | NT | NT |
| HUT-102 | >100 | >100 | NT | NT | >100 | NT | >100 | NT | NT | NT | NT |
| Cells from patient |  |  |  |  |  |  |  |  |  |  |  |
| MM-1 | NT | NT | NT | NT | 0.4 | NT | NT | NT | NT | NT | NT |
| MM-2 | NT | NT | NT | NT | 17.0 | NT | NT | NT | NT | NT | NT |
| MM-3 | NT | NT | NT | NT | 2.3 | NT | NT | NT | NT | NT | NT |
| MM-4 | NT | NT | NT | NT | 17.9 | NT | NT | NT | NT | NT | NT |

NT = not tested

Example 7

This example demonstrates the cytotoxicity of anti-BCMA immunotoxin at a fixed dose.

To test whether LMB38 and LMB70 actually kill the cells rather than merely inhibit growth, the BCMA-positive H929 cells were incubated with no toxin (control (Ctrl)) or 100 ng/ml of LMB38 or LMB70 for 2 hrs, 4 hrs, 6 hrs or 24 hrs followed by washing and incubation on fresh media. Cell killing activity was measured by trypan blue staining of cells taken at various time points (days) after exposure to the immunotoxin. As shown in Tables 4A and 4B, the cells were all dead (trypan blue positive) even after 2 hours of exposure to 100 ng/ml of LMB38. The cells did not revive after 21 days, indicating that the cells were all dead upon exposure to 100 ng/ml of LMB38.

TABLE 4A

| Cell | Percent dead | | | |
|---|---|---|---|---|
| LMB38 | Day (D)-1 | D-2 | D-5 | D-7 |
| H929-Cntrl | 6 | 10 | 25 | 27 |
| H929-2 hr | 46 | 84 | 98 | 100 |
| H929-4 hr | 44 | 85 | 100 | 100 |
| H929-6 hr | 48 | 87 | 100 | 100 |
| H929-24 hr | 50 | 94 | 100 | 100 |

TABLE 4B

| Cell | Percent dead | | | |
|---|---|---|---|---|
| LMB70 | D-1 | D-2 | D-5 | D-7 |
| H929-Cntrl | 3 | 4 | 29 | 35 |
| H929-2 hr | 43 | 88 | 100 | 100 |
| H929-4 hr | 44 | 89 | 100 | 100 |
| H929-6 hr | 42 | 88 | 100 | 100 |
| H929-24 hr | 51 | 95 | 100 | 100 |

The BCMA-positive H929, U266, and RPMI cell lines were seeded at 10$^6$ per ml in 3 ml volume. LMB38 (BM24-Fab-LRggs) was added at 100 ng/ml at Day 0 (D-0). Cells (10 µl) were taken on different days and counted after trypan blue staining. After D-3, cells were washed and plated with media containing no toxin. For the 6 hour group, cells were washed after 6 h and plated in regular media containing no toxin. Cyclohexamide (Chxm) and 205 were used as positive controls; SS1-Fab-immunotoxin targeting mesothelin was used as a negative control (Ctrl).

As shown in Table 5, all three cell lines were killed by LMB38 at a high dose.

TABLE 5

| Cell | Percent dead | | | | | | |
|---|---|---|---|---|---|---|---|
|  | D-0 | D-1 | D-2 | D-3 | D-6 | D-8 | D-21 |
| H929-Cntrl | 12 | 19 | 24 | 23 | 25 | NT | NT |
| H929-LMB38 | 10 | 62 | 97 | 100 | 100 | 100 | 100 |
| H929-6 hr | 13 | 87 | 100 | 100 | 100 | 100 | 100 |
| H929-Chxm | 9 | 70 | 92 | 100 | 100 | NT | NT |
| H929-205 | 14 | NT | NT | 27 | NT | NT | NT |
| U266B-Cntrl | 2 | 3 | 4 | 12 | 14 | NT | NT |
| U266-LMB38 | 5 | 23 | 59 | 90 | 100 | 100 | 100 |
| U266B-6 hr | 4 | 25 | 74 | 95 | 100 | 100 | 100 |
| U266B-Chxm | 7 | 25 | 50 | 80 | 100 | NT | NT |
| U266B-205 | 10 | NT | NT | 18 | NT | NT | NT |
| RPMI-Ctrl | 10 | 15 | 20 | 25 | 30 | NT | NT |
| RPMI-LMB38 | 12 | 60 | 100 | 100 | 100 | 100 | 100 |
| RPMI-6 hr | 9 | 75 | 90 | 98 | 100 | 100 | 100 |
| RPMI-Chmx | 15 | 75 | 100 | 100 | 100 | NT | NT |
| RPMI-205 | 18 | NT | NT | 28 | NT | NT | NT |

NT = not tested.

Example 8

This example demonstrates the antitumor activity of LMB38 in mice with H929 xenograft tumors.

To test the in vivo efficacy of LMB38 and LMB70, tumors were grown in SCID mice using the most sensitive cell line H929. Based on the previous toxicity data, 1.5 mg/kg QODX5 doses were used on 5 mice in each group. As shown in FIGS. 1A and 1B, the tumor growth in immunotoxin-treated groups was delayed as compared to control phosphate buffered saline (PBS)-treated mice. However, the tumors grew back once the treatment was finished.

Example 9

This example demonstrates the antitumor activity of the combination of LMB70 and abraxane in mice with H929 xenograft tumors.

The sensitivity of H929 and U266B cells to abraxane and bortezumib (BTZ) was measured in vitro. The results are shown in Table 6.

TABLE 6

|  | Abraxane IC$_{50}$ | BTZ IC$_{50}$ |
|---|---|---|
| H929 | 0.5 ng/ml | 4 nM |
| U266B | 1.0 ng/ml | NT |

NT = not tested

Tumors were grown in mice using the cell line H929. When the tumors reached a volume of about 100 mm$^3$, the mice were administered control (vehicle), LMB70 only, abraxane only, or a combination of abraxane (Abrx) and LMB70. The dosage was: LMB70 (BM306-Fab-LR-ggs): 1 mg/kg QODX5; Abrx: 40 mg/kg X1.

Figure 2:
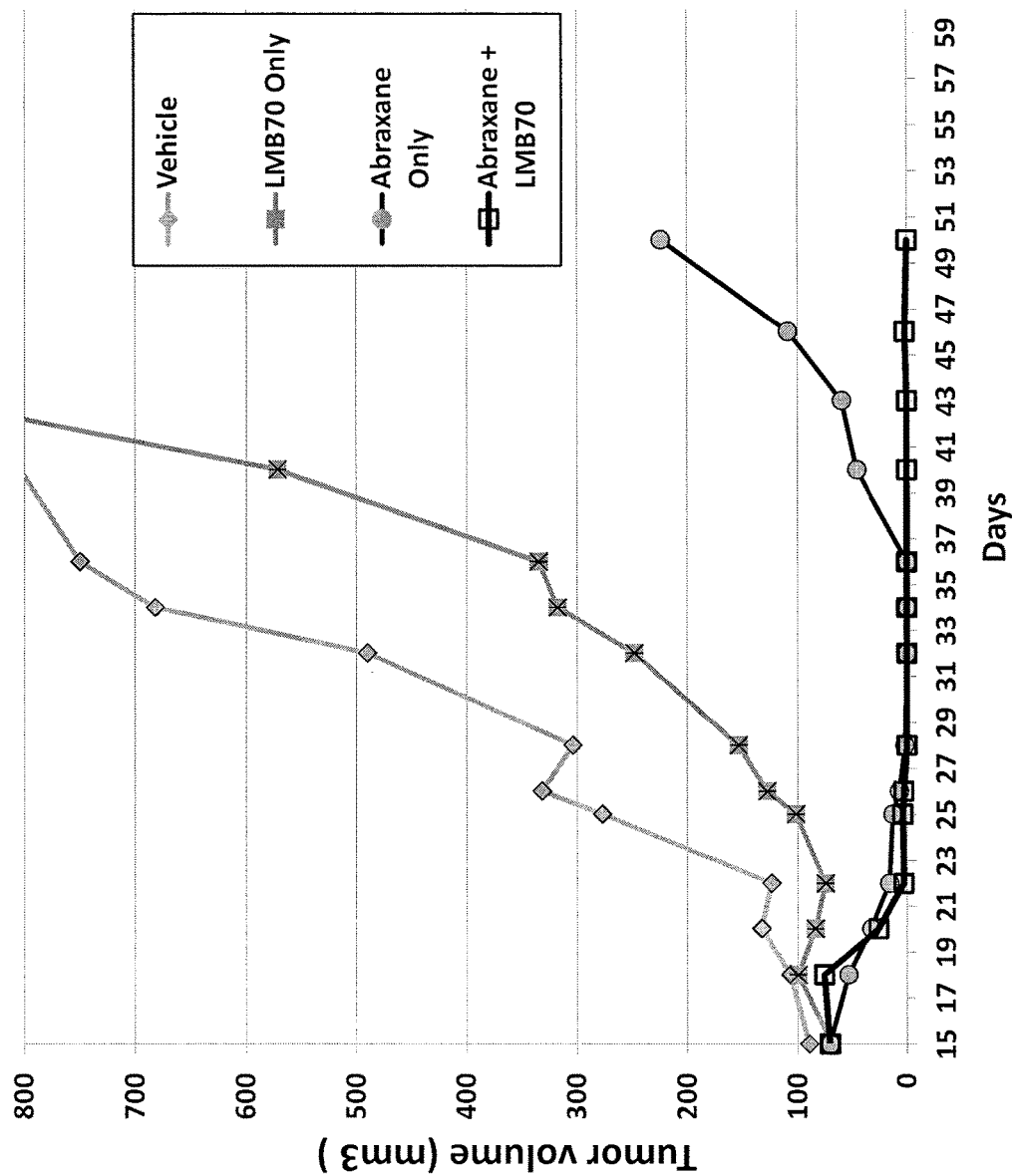
FIG. 2 is a graph showing the tumor volume ($mm^3$) in mice treated with control (vehicle) (diamonds), LMB70 only (closed squares), abraxane only (circles), or a combination of abraxane and LMB70 (open squares) at various time points (days) after the mice were injected with tumor cells. Immunotoxin was administered to the mice on Days 15, 16, 18, 20, 23, and 25.
Figure 3A:
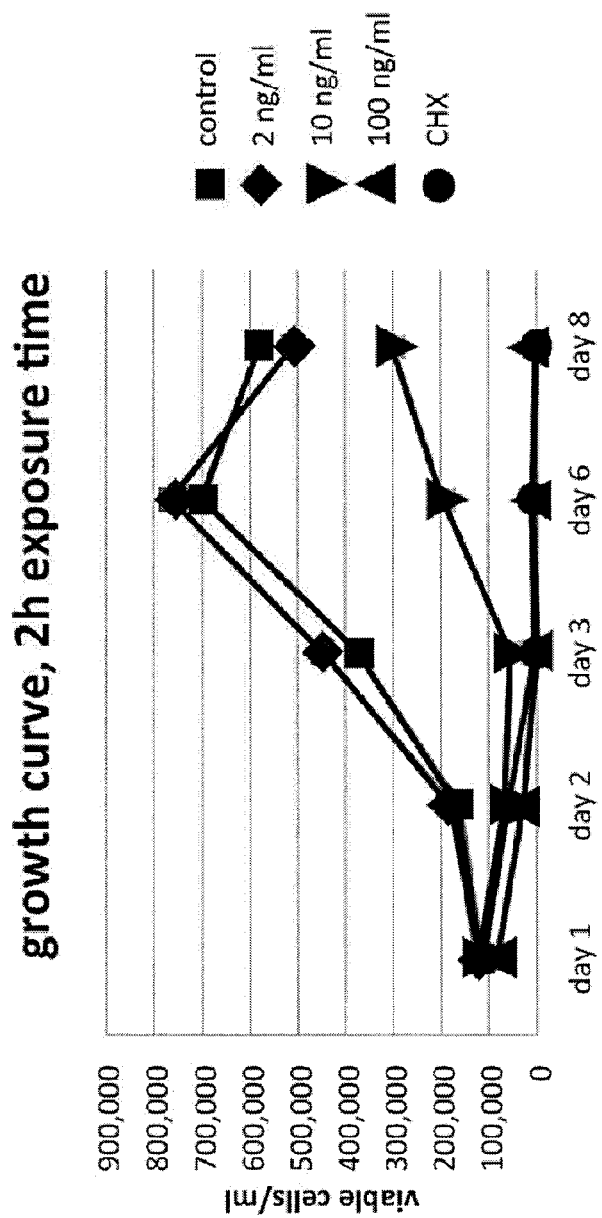
FIG. 3A is a graph showing the number of viable cells/ml at various time points (days) after a 2 hour exposure to control (squares), 2 ng/ml LMB70 (diamonds), 10 ng/ml LMB70 (▼), 100 ng/ml LMB70 (▲), or CHX (circles).
Figure 3B:
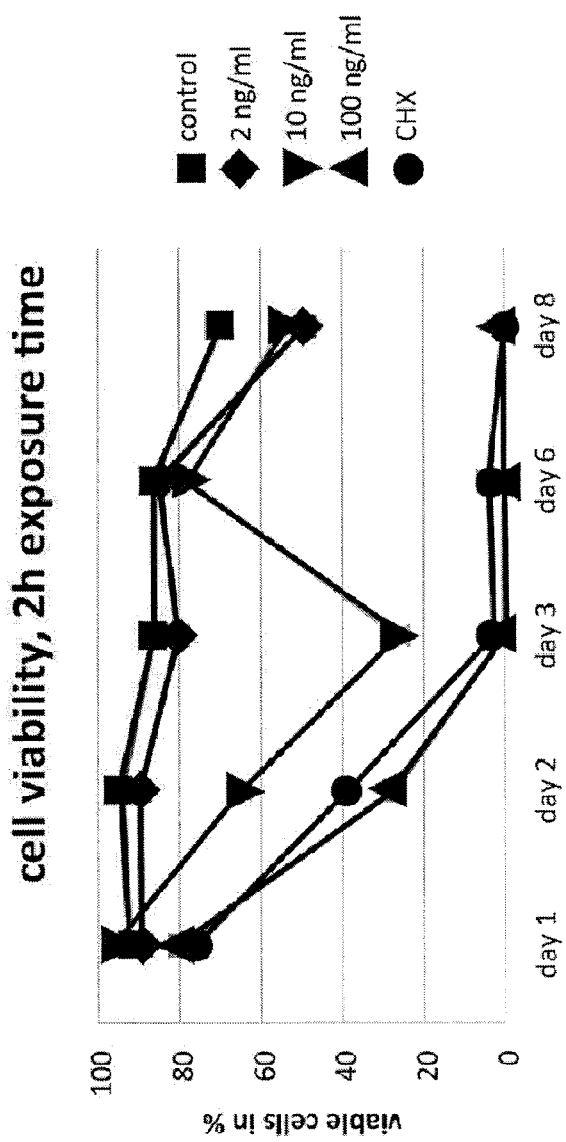
FIG. 3B is a graph showing percentage of viable cells at various time points (days) after a 2 hour exposure to control (squares), 2 ng/ml LMB70 (diamonds), 10 ng/ml LMB70 (▼), 100 ng/ml LMB70 (▲), or CHX (circles).
Figure 3C:
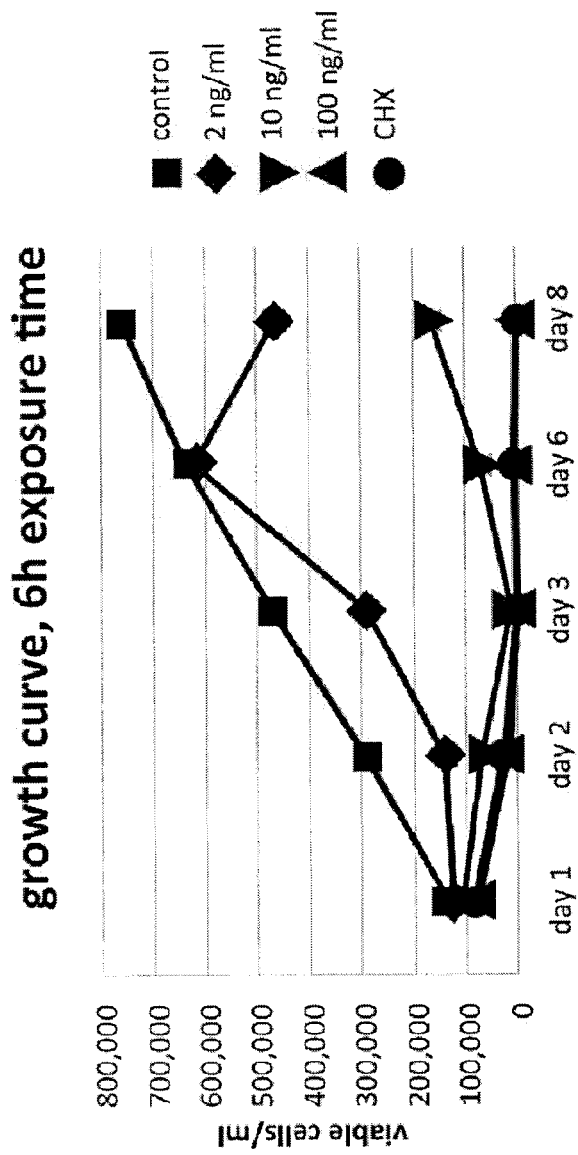
FIG. 3C is a graph showing the number of viable cells/ml at various time points (days) after a 6 hour exposure to control (squares), 2 ng/ml LMB70 (diamonds), 10 ng/ml LMB70 (▼), 100 ng/ml LMB70 (▲), or CHX (circles).
Figure 3D:
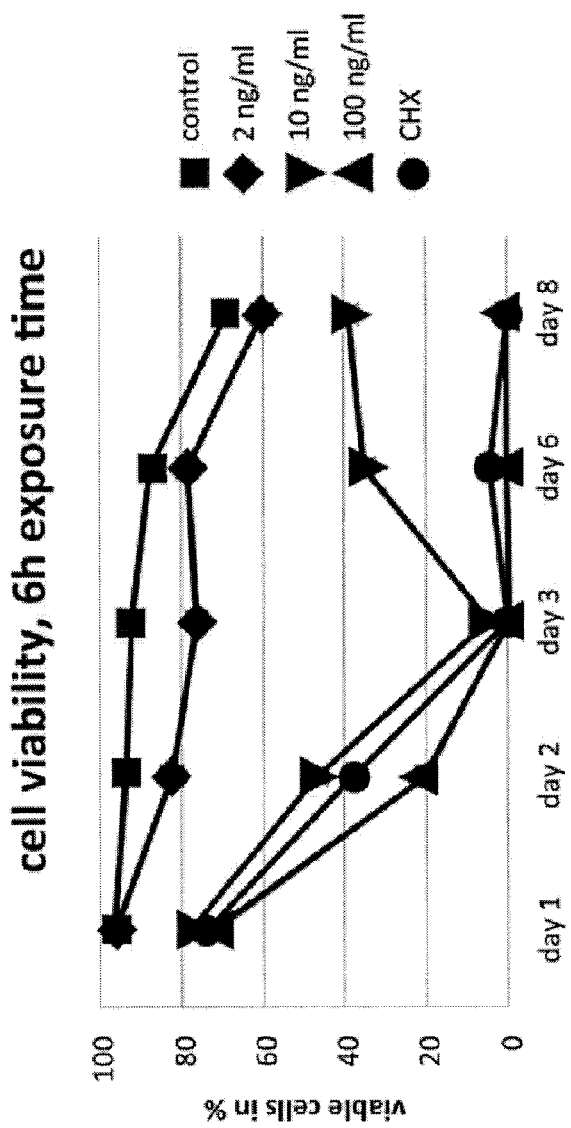
FIG. 3D is a graph showing percentage of viable cells at various time points (days) after a 6 hour exposure to control (squares), 2 ng/ml LMB70 (diamonds), 10 ng/ml LMB70 (▼), 100 ng/ml LMB70 (▲), or CHX (circles).
Figure 4A:
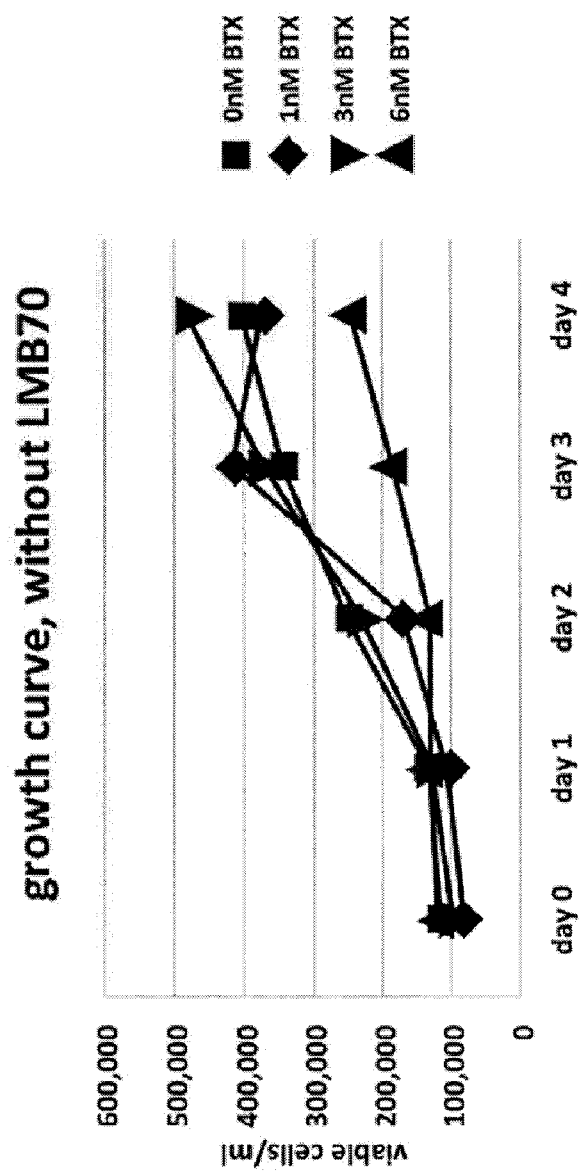
FIG. 4A is a graph showing the number of viable cells/ml at various time points (days) after a 4 hour exposure to 0 nM bortezomib (BTX) (squares), 1 nM BTX (diamonds), 3 nM BTX (▼), or 6 nM BTX alone (no toxin) (▲).
Figure 4B:
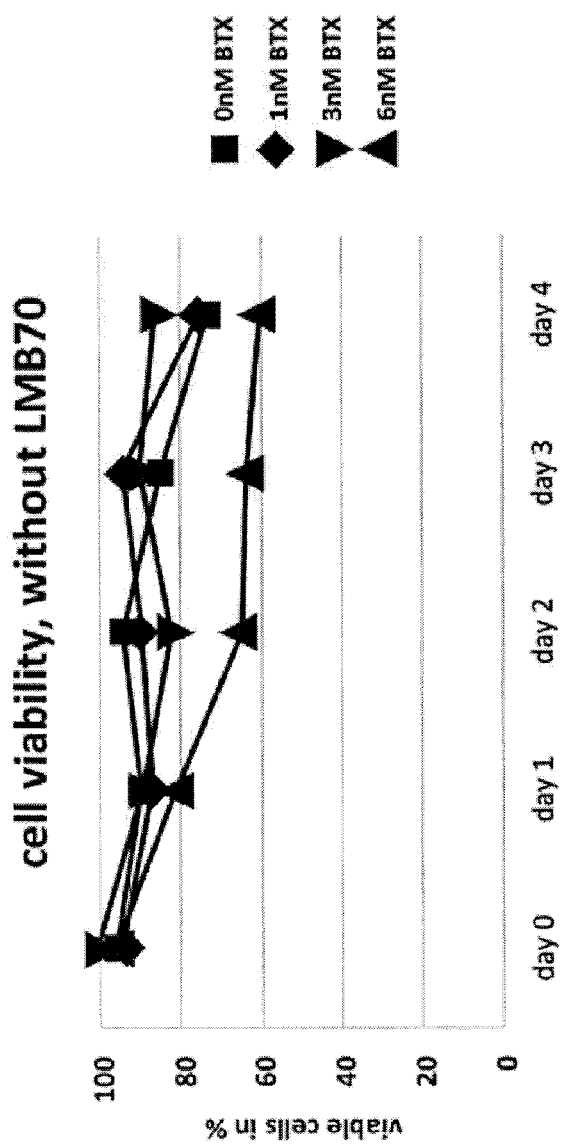
FIG. 4B is a graph showing the percentage of viable cells at various time points (days) after a 4 hour exposure to 0 nM bortezomib (BTX) (squares), 1 nM BTX (diamonds), 3 nM BTX (▼), or 6 nM BTX alone (no toxin) (▲).
Figure 4C:
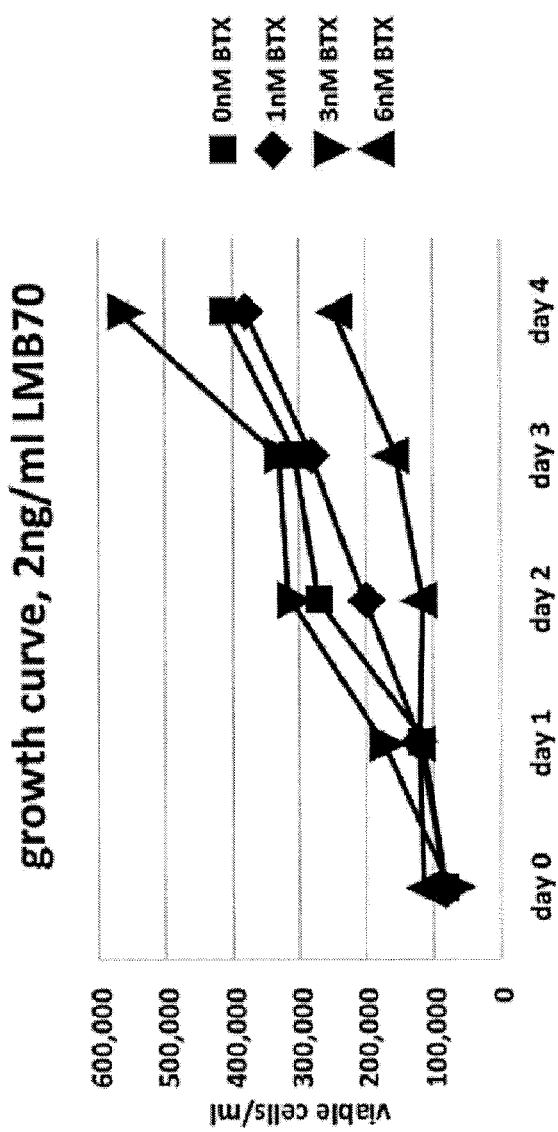
FIG. 4C is a graph showing the number of viable cells/ml at various time points (days) after a 4 hour exposure to 0 nM bortezomib (BTX) (squares), 1 nM BTX (diamonds), 3 nM BTX (▼), or 6 nM BTX (▲) in combination with 2 ng/ml LMB70.
Figure 4D:
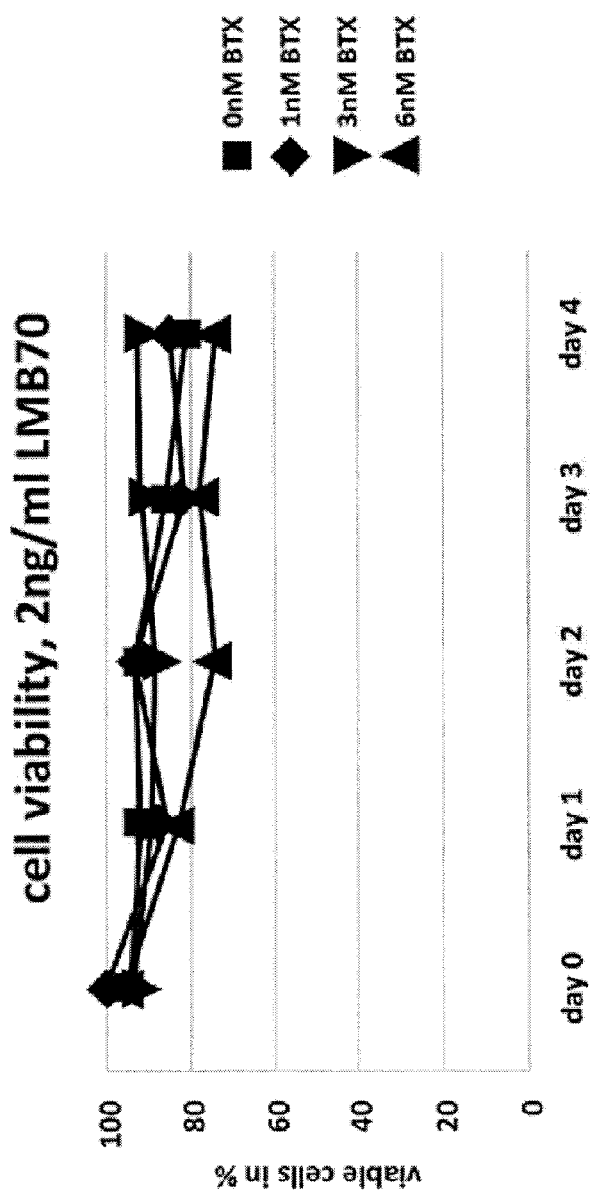
FIG. 4D is a graph showing the percentage of viable cells at various time points (days) after a 4 hour exposure to 0 nM bortezomib (BTX) (squares), 1 nM BTX (diamonds), 3 nM BTX (▼), or 6 nM BTX (▲) in combination with 2 ng/ml LMB70.
Figure 5A:
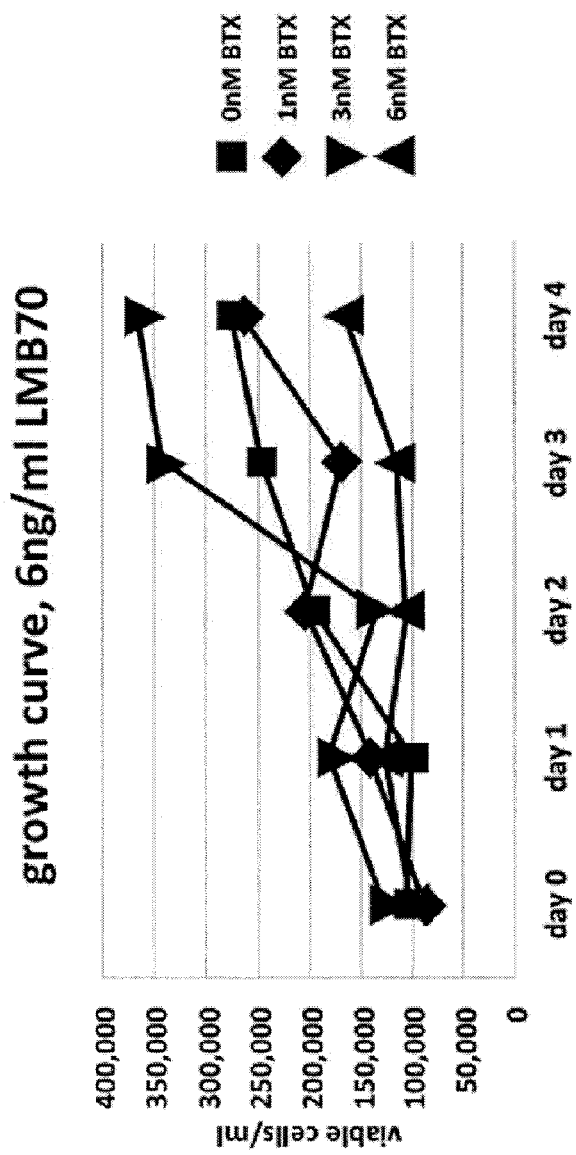
FIG. 5A is a graph showing the number of viable cells/ml at various time points (days) after a 4 hour exposure to 0 nM bortezomib (BTX) (squares), 1 nM BTX (diamonds), 3 nM BTX (▼), or 6 nM BTX (▲) in combination with 6 ng/ml LMB70.
Figure 5B:
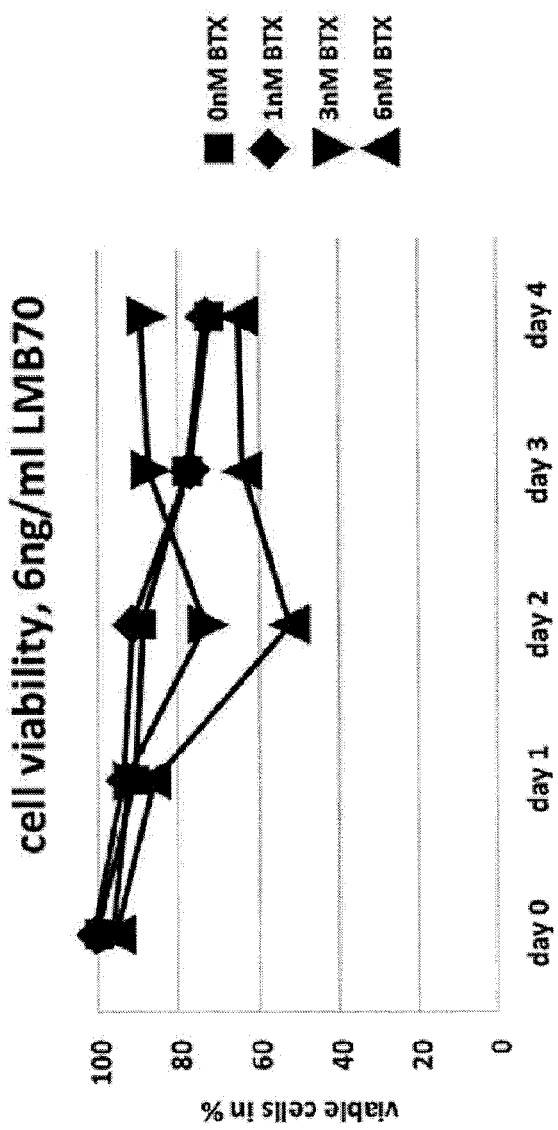
FIG. 5B is a graph showing the percentage of viable cells at various time points (days) after a 4 hour exposure to 0 nM bortezomib (BTX) (squares), 1 nM BTX (diamonds), 3 nM BTX (▼), or 6 nM BTX (▲) in combination with 6 ng/ml LMB70.
Figure 5C:
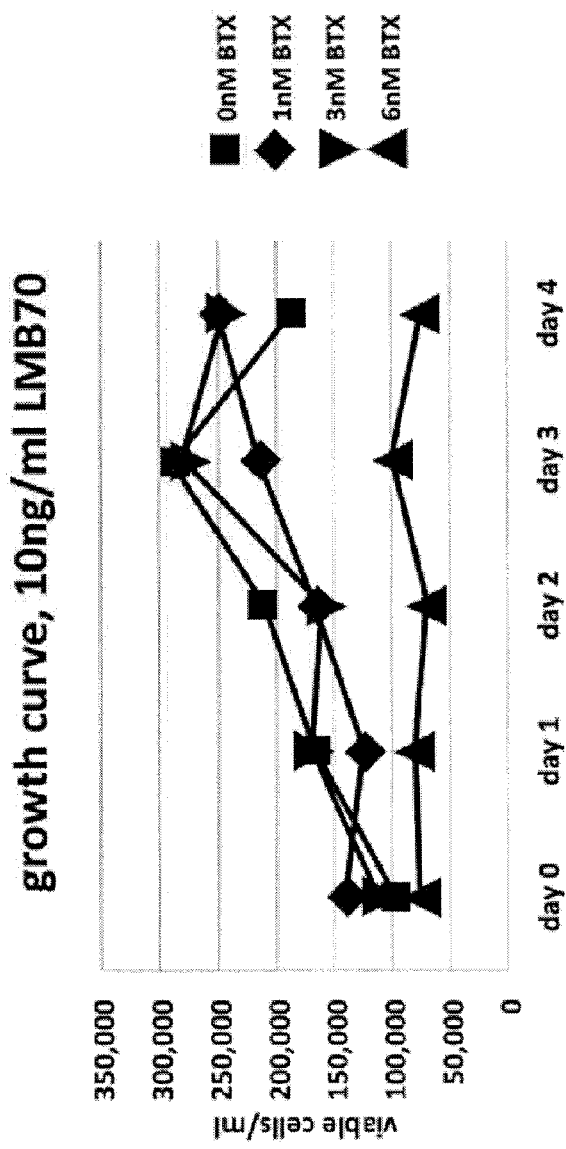
FIG. 5C is a graph showing the number of viable cells/ml at various time points (days) after a 4 hour exposure to 0 nM bortezomib (BTX) (squares), 1 nM BTX (diamonds), 3 nM BTX (▼), or 6 nM BTX (▲) in combination with 10 ng/ml LMB70.
Figure 5D:
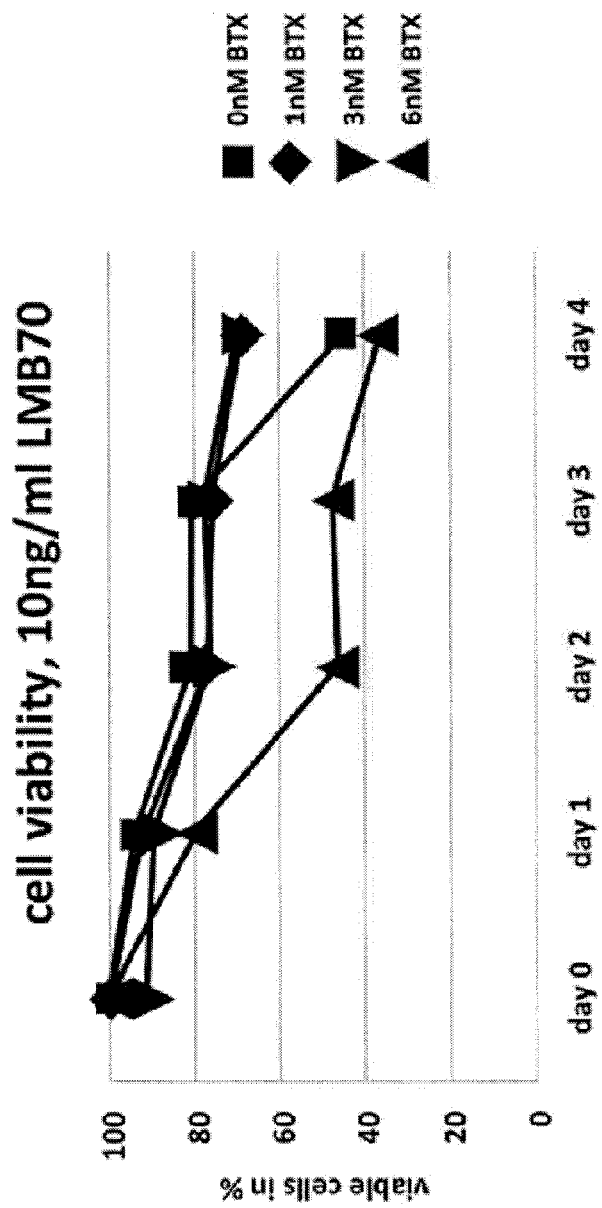
FIG. 5D is a graph showing the percentage of viable cells at various time points (days) after a 4 hour exposure to 0 nM bortezomib (BTX) (squares), 1 nM BTX (diamonds), 3 nM BTX (▼), or 6 nM BTX (▲) in combination with 10 ng/ml LMB70.

Tumor volume was measured. The results are shown in FIG. 2. As shown in FIG. 2, tumor growth was inhibited in mice treated with the combination of abraxane and LMB70.

Example 10

This example demonstrates the duration of exposure to LMB70 needed to kill H929 cells. This example also demonstrates how fast the H929 cells die after exposure to LMB70.

LMB70 was labeled with AF647 for measurement of uptake in vivo. LMB70 was labeled twice with AF647 using an AF647 labeling kit (Life Technologies). Labeling efficacy and activity were measured by WST-8 assay and affinity measurement. WST-8 analysis after the first labeling revealed an 10$_{50}$ of 1.532 for the unlabeled LMB70 and 6.082 for the labeled LMB70. WST-8 analysis after the second labeling revealed an IC$_{50}$ of 2.758 for the unlabeled LMB70 and 10.69 for the labeled LMB70. Affinity measurement after the first labeling revealed a Bmax of 2220 for the unlabeled LMB70 and 1131 for the labeled LMB70 and a Kd of 4078 for the unlabeled LMB70 and 3673 for the labeled LMB70. It was determined that the labeled toxins were about 4-fold less active than the unlabeled toxins.

To quantify the BCMA molecules on the surface of H929 cells, H929 cells were incubated with various concentrations of labeled LMB70 for 1h on ice in FLOW buffer. The cells were washed and analyzed by flow cytometry, together with AF647 quantification beads. The results showed that after the first labeling, the Bmax was 150,000 molecules per cell and the Kd was 710 ng/ml (9.5 nM). After the second labeling, the Bmax was 230,000 molecules per cell, and the Kd was 1600 ng/ml (21 nM).

H929 cells were exposed to LMB70 for various durations. Cell viability was analyzed after 3 days by flow cytometry (Annexin V/7AAD staining). The results showed that, with a high dose of LMB70 (100 ng/ml), very short exposure times (e.g., as short as 10 minutes) are sufficient to kill cells.

H929 cells were exposed to 100 ng/ml LMB70 for 20 minutes. Cell viability was analyzed with trypan blue staining. The results showed that the H929 cells started to die 24 h after exposure, and all cells were dead after 3 days.

H929 cells were exposed to 2 ng/ml LMB70 for various lengths of time from 10 minutes up to 72 hours. Cell viability was analyzed after 3 days by flow cytometry (Annexin V/7AAD staining). The results showed that with 2 ng/ml LMB70, the cells did not die, even after 24 hours of exposure.

Example 11

This example demonstrates the effect of varying concentrations of LMB70 on H929 cell viability and growth.

H929 cells were exposed to 2, 10, and 100 ng/ml LMB70 for 2 hours or 6 hours. Cell viability and cell density were analyzed. The results are shown in FIGS. 3A-3D. The results showed that 2 ng/ml LMB70 only provided slight growth inhibition, but no cell killing. 10 ng/ml LMB70 was not enough to kill all cells; the surviving cells grew out after some time.

H929 cells were exposed to 0, 2, 6 or 10 ng/ml LMB70 in combination with 0, 1, 3 or 6 nM Botezomib for 4h. Cell viability and cell density were analyzed with trypan blue staining. The results are shown in FIGS. 4A-4D and 5A-5D.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A polypeptide comprising an antigen binding domain of an antibody, the antigen binding domain comprising the heavy chain complementarity determining region (CDR) 1 amino acid sequence of SEQ ID NO: 7, the heavy chain CDR2 amino acid sequence of SEQ ID NO: 8, the heavy chain CDR3 amino acid sequence of SEQ ID NO: 9, the light chain CDR1 amino acid sequence of SEQ ID NO: 10, the light chain CDR2 amino acid sequence of SEQ ID NO: 11, and the light chain CDR3 amino acid sequence of SEQ ID NO: 12, wherein the antigen binding domain specifically binds to human B-cell Maturation Antigen (BCMA).

2. The polypeptide of claim 1, wherein the antigen binding domain comprises the amino acid sequences of SEQ ID NOs: 15-16.

3. An antibody, or an antigen-binding portion of the antibody, comprising the heavy chain complementarity determining region (CDR) 1 amino acid sequence of SEQ ID NO: 7, the heavy chain CDR2 amino acid sequence of SEQ ID NO: 8, the heavy chain CDR3 amino acid sequence of SEQ ID NO: 9, the light chain CDR1 amino acid sequence of SEQ ID NO: 10, the light chain CDR2 amino acid sequence of SEQ ID NO: 11, and the light chain CDR3 amino acid sequence of SEQ ID NO: 12,
wherein the antibody and the antigen-binding portion of the antibody specifically bind to human B-cell Maturation Antigen (BCMA).

4. The antibody, or the antigen-binding portion of the antibody, of claim 3, wherein the antibody, or the antigen-binding portion of the antibody is an antibody, Fab fragment (Fab), F(ab')$_2$ fragment, diabody, triabody, or tetrabody.

5. The antibody, or the antigen-binding portion of the antibody, of claim 3, wherein the antibody is a bispecific antibody.

6. A chimeric antigen receptor (CAR) comprising the polypeptide of claim 1.

7. A conjugate comprising (a) the antibody, or the antigen-binding portion of the antibody, of claim 3 conjugated or fused to (b) an effector molecule.

8. The conjugate of claim 7, wherein the effector molecule is a drug, toxin, label, small molecule, or an antibody.

9. The conjugate of claim 7, wherein the effector molecule is (i) *Pseudomonas* exotoxin A (PE), (ii) a cytotoxic fragment of PE, or (iii) a cytotoxic variant of (i) or (ii).

10. The conjugate of claim 7, wherein the effector molecule is selected from the group consisting of PE-LR, PE-LO10R456A, PE-T20, PE-T20-KDEL, PE4E, PE40, PE38, PE 24, PE25, PE38QQR, PE38KDEL, and PE35.

11. The conjugate of claim 7, wherein the effector molecule is conjugated or fused to the antibody, or the antigen-binding portion of the antibody, via a linker.

12. The conjugate of claim 11, wherein the linker comprises the amino acid sequence of SEQ ID NO: 17 or 18.

13. A nucleic acid encoding the antibody, or the antigen-binding portion of the antibody, of claim 3.

14. A recombinant expression vector comprising the nucleic acid of claim 13.

15. A host cell comprising the recombinant expression vector of claim 14.

16. A population of host cells comprising at least two host cells of claim 15.

17. A pharmaceutical composition comprising the antibody, or the antigen-binding portion of the antibody, of claim 3 and a pharmaceutically acceptable carrier.

18. A method of detecting the presence of B cell maturation antigen (BCMA) on a cell or cells from a human, the method comprising:
(a) contacting one or more cells from the human with the polypeptide of claim 1, thereby forming a complex in which the polypeptide specifically binds to human BCMA if present, and
(b) detecting the complex.

19. The method of claim 18, wherein the cell or cells is/are from a human having cancer, wherein the cancer is Burkitt's lymphoma, diffuse large B-cell lymphoma (DLBCL) lymphoma, acute lymphocytic leukemia (ALL) lymphoma, Hodgkin's lymphoma or multiple myeloma.

20. A method of treating a BCMA positive cancer in a mammal, the method comprising administering to the mammal a conjugate in an amount sufficient to treat the BCMA positive cancer in the mammal,
wherein the conjugate comprises (a) a toxin conjugated or fused to (b) an antibody, or an antigen-binding portion of the antibody, comprising the heavy chain complementarity determining region (CDR) 1 amino acid sequence of SEQ ID NO: 7, the heavy chain CDR2 amino acid sequence of SEQ ID NO: 8, the heavy chain CDR3 amino acid sequence of SEQ ID NO: 9, the light chain CDR1 amino acid sequence of SEQ ID NO: 10, the light chain CDR2 amino acid sequence of SEQ ID NO: 11, and the light chain CDR3 amino acid sequence of SEQ ID NO: 12,
wherein the antibody and the antigen-binding portion of the antibody specifically bind to human B-cell Maturation Antigen (BCMA) expressed by the cancer cells.

21. The method of claim 20, wherein the cancer is Burkitt's lymphoma, DLBCL lymphoma, ALL lymphoma, Hodgkin's lymphoma or multiple myeloma.

22. The method of claim 20, further comprising administering a second therapeutic agent to the mammal.

23. The antibody, or the antigen-binding portion of the antibody, of claim 3, comprising the amino acid sequences of SEQ ID NOs: 15-16.

24. The polypeptide of claim 1, wherein the polypeptide is a single-chain variable region fragment (scFv) or disulfide-stabilized variable region fragment (dsFv).

25. A conjugate comprising (a) the polypeptide of claim 1, conjugated or fused to (b) an effector molecule.

* * * * *